United States Patent
Perez et al.

(10) Patent No.: US 11,552,952 B1
(45) Date of Patent: *Jan. 10, 2023

(54) PROVIDING NOTIFICATIONS TO AUTHORIZED USERS

(71) Applicant: C/HCA, Inc., Nashville, TN (US)

(72) Inventors: Gabriel O. Perez, Fort Lauderdale, FL (US); Michael A. Houston, Mentone, AL (US); David Fowler, Brentwood, TN (US); Milind Madhukar Borkar, Franklin, TN (US); Thomas Andrew Doyle, Franklin, TN (US); Alan Scott, Franklin, TN (US); William Michael Gregg, Nashville, TN (US); Jim Najib Jirjis, Nashville, TN (US); Jonathan Perlin, Nashville, TN (US); Paul Martin Paslick, Nashville, TN (US); Paul Currie, Franklin, TN (US)

(73) Assignee: C/HCA, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/731,937

(22) Filed: Dec. 31, 2019

Related U.S. Application Data

(63) Continuation of application No. 15/980,575, filed on May 15, 2018, now Pat. No. 10,542,004, which is a
(Continued)

(51) Int. Cl.
| | | |
|---|---|---|
| *G06F 21/00* | (2013.01) | |
| *H04L 9/40* | (2022.01) | |
| *G16H 40/20* | (2018.01) | |
| *G16H 10/60* | (2018.01) | |
| *G16H 50/20* | (2018.01) | |

(Continued)

(52) U.S. Cl.
CPC .............. *H04L 63/10* (2013.01); *G06F 9/451* (2018.02); *G06F 21/604* (2013.01); *G16H 10/60* (2018.01); *G16H 40/20* (2018.01); *G16H 50/20* (2018.01); *G16H 80/00* (2018.01); *H04L 51/214* (2022.05); *H04L 51/224* (2022.05); *H04L 63/0428* (2013.01); *H04L 63/08* (2013.01); *H04L 63/166* (2013.01); *H04L 63/0407* (2013.01)

(58) Field of Classification Search
None
See application file for complete search history.

(56) References Cited

U.S. PATENT DOCUMENTS

| | | |
|---|---|---|
| 5,735,285 A | 4/1998 | Albert et al. |
| 6,385,589 B1 | 5/2002 | Trusheim et al. |

(Continued)

*Primary Examiner* — Maung T Lwin
(74) *Attorney, Agent, or Firm* — Kilpatrick Townsend & Stockton, LLP

(57) ABSTRACT

A method and system for initiating message listening and routing message content to authorized user devices is disclosed. For a second user device to receive notifications regarding records of a first user, the second user device provides information identifying the first user to a notification service. The notification service verifies the identifying information. The notification service initiates one or more listeners to listen for messages flowing over a messaging bus that are relating to the first user. Once a message is identified, at least a portion of the message is used to generate a notification that may be sent to the second user device.

14 Claims, 13 Drawing Sheets

Related U.S. Application Data continuation-in-part of application No. 15/896,788, filed on Feb. 14, 2018, now Pat. No. 10,505,935, which is a continuation of application No. 14/954,249, filed on Nov. 30, 2015, now Pat. No. 9,906,532, which is a continuation of application No. 14/630,393, filed on Feb. 24, 2015, now Pat. No. 9,203,814, said application No. 15/980,575 is a continuation-in-part of application No. 15/476,243, filed on Mar. 31, 2017, now Pat. No. 9,973,455.

(60) Provisional application No. 61/943,871, filed on Feb. 24, 2014, provisional application No. 62/316,213, filed on Mar. 31, 2016.

(51) Int. Cl.
*G06F 21/60* (2013.01)
*G06F 9/451* (2018.01)
*G16H 80/00* (2018.01)
*H04L 51/214* (2022.01)
*H04L 51/224* (2022.01)

(56) References Cited

U.S. PATENT DOCUMENTS

| | | | |
|---|---|---|---|
| 6,730,026 B2 * | 5/2004 | Christ | G16H 20/10 128/920 |
| 6,952,181 B2 | 10/2005 | Karr et al. | |
| 7,644,168 B2 | 1/2010 | Grieff et al. | |
| 7,654,965 B2 * | 2/2010 | Morganroth | G16H 15/00 705/3 |
| 7,742,762 B1 | 6/2010 | Biere et al. | |
| 7,853,241 B1 | 12/2010 | Harrison | |
| 7,899,764 B2 * | 3/2011 | Martin | G16H 30/20 706/12 |
| 8,005,692 B2 | 8/2011 | Demetrios et al. | |
| 8,160,895 B2 * | 4/2012 | Schmitt | G06Q 10/10 705/2 |
| 8,731,969 B1 * | 5/2014 | Bellam | G16H 10/60 705/3 |
| 8,862,393 B2 * | 10/2014 | Zhou | G01S 19/17 701/468 |
| 8,954,472 B1 | 2/2015 | Chapman et al. | |
| 9,203,814 B2 | 12/2015 | Perez et al. | |
| 9,558,332 B1 * | 1/2017 | Keiser | G06F 21/6209 |
| 9,906,532 B2 | 2/2018 | Preez et al. | |
| 9,973,455 B1 | 5/2018 | Fowler et al. | |
| 10,505,935 B1 * | 12/2019 | Perez | G06F 21/604 |
| 10,542,004 B1 | 1/2020 | Perez | H04L 63/166 |
| 2002/0016719 A1 | 2/2002 | Nemeth et al. | |
| 2002/0026339 A1 * | 2/2002 | Frankland | G06Q 10/063 707/E17.108 |
| 2002/0065685 A1 | 5/2002 | Sasaki et al. | |
| 2003/0215092 A1 | 11/2003 | Dick | |
| 2004/0193068 A1 * | 9/2004 | Burton | A61B 5/369 600/595 |
| 2004/0249674 A1 | 12/2004 | Eisenberg et al. | |
| 2005/0063365 A1 | 3/2005 | Mathew et al. | |
| 2005/0076110 A1 | 4/2005 | Mathew et al. | |
| 2005/0108052 A1 * | 5/2005 | Omaboe | G16H 40/20 705/2 |
| 2005/0151640 A1 | 7/2005 | Hastings | |
| 2005/0283198 A1 * | 12/2005 | Haubrich | A61N 1/37282 607/30 |
| 2007/0067185 A1 * | 3/2007 | Halsted | G06F 19/00 705/2 |
| 2007/0197195 A1 * | 8/2007 | Sugiyama | G06Q 30/02 455/412.2 |
| 2008/0022370 A1 * | 1/2008 | Beedubail | H04L 63/101 726/4 |
| 2008/0046292 A1 * | 2/2008 | Myers | G06F 16/283 705/3 |
| 2008/0140484 A1 * | 6/2008 | Akerman | G06Q 10/063 705/7.11 |
| 2008/0201174 A1 * | 8/2008 | Ramasubramanian | G16H 20/10 705/3 |
| 2008/0228522 A1 * | 9/2008 | Davis | G16H 50/20 705/2 |
| 2008/0294507 A1 | 11/2008 | Reiner | |
| 2009/0037224 A1 | 2/2009 | Raduchel | |
| 2009/0113560 A1 | 4/2009 | Kori et al. | |
| 2010/0024021 A1 * | 1/2010 | Heath | G16H 15/00 726/7 |
| 2011/0129131 A1 | 6/2011 | Avinash et al. | |
| 2012/0089481 A1 | 4/2012 | Iozzia et al. | |
| 2012/0165620 A1 | 6/2012 | Tanis et al. | |
| 2012/0180122 A1 | 7/2012 | Yan et al. | |
| 2012/0182924 A1 | 7/2012 | Gaines et al. | |
| 2012/0185268 A1 * | 7/2012 | Wiesner | H04B 7/15542 705/2 |
| 2012/0215560 A1 * | 8/2012 | Ofek | G16H 10/00 705/3 |
| 2013/0173305 A1 | 7/2013 | Hyde et al. | |
| 2013/0218599 A1 * | 8/2013 | Highley | G06Q 10/10 705/3 |
| 2013/0262357 A1 * | 10/2013 | Amarasingham | G16H 50/70 706/21 |
| 2014/0022080 A1 | 1/2014 | Mayoras. | |
| 2014/0067427 A1 | 3/2014 | Demopulos | |
| 2014/0074509 A1 * | 3/2014 | Amarasingham | G16H 50/30 705/3 |
| 2014/0081667 A1 | 3/2014 | Joao | |
| 2014/0180711 A1 | 6/2014 | Kamen et al. | |
| 2014/0316797 A1 * | 10/2014 | Biernacki | G16H 50/30 705/2 |
| 2015/0244687 A1 | 8/2015 | Perez et al. | |
| 2015/0304300 A1 * | 10/2015 | Bender | H04L 12/1895 726/4 |

* cited by examiner

PROVIDING NOTIFICATIONS TO AUTHORIZED USERS

CROSS-REFERENCES TO RELATED APPLICATIONS

The present application is a continuation of U.S. application Ser. No. 15/980,575, filed May 15, 2018, and entitled "PROVIDING NOTIFICATIONS TO AUTHORIZED USERS," which is a continuation-in-part of U.S. application Ser. No. 15/896,788, filed Feb. 14, 2018, issued as U.S. Pat. No. 10,505,935, and entitled "PROVIDING NOTIFICATIONS TO AUTHORIZED USERS," which is a continuation of U.S. application Ser. No. 14/954,249, filed Nov. 30, 2015, issued as U.S. Pat. No. 9,906,532, and entitled "PROVIDING NOTIFICATIONS TO AUTHORIZED USERS," which is a continuation of U.S. application Ser. No. 14/630,393, filed Feb. 24, 2015, issued as U.S. Pat. No. 9,203,814, and entitled "PROVIDING NOTIFICATIONS TO AUTHORIZED USERS," which claims the benefit of U.S. Application No. 61/943,871, filed on Feb. 24, 2014, and entitled "MEDICAL MESSAGING SYSTEM." U.S. application Ser. No. 15/980,575 is also a continuation-in-part of U.S. application Ser. No. 15/476,243, filed Mar. 31, 2017, issued as U.S. Pat. No. 9,973,455, entitled "MESSAGE CUSTOMIZATION AND ROUTING," which claims the benefit of U.S. Application No. 62/316,213, filed Mar. 31, 2016, entitled "HEALTH INFORMATION EXCHANGE SERVICE BUS". The entire disclosures of the above applications are hereby incorporated by reference, for all purposes, as if fully set forth herein.

This specification relates in general to notification systems and, but not by way of limitation, to initiating message listening and routing message content to authorized user devices.

A record management system may manage records for many different users. In some cases, some of the records are adjustable by entities internal to the record management system and to other entities external to the record management system. In any event, a user to whom the record belongs may be interested in receiving a notification when a record is adjusted (e.g., changed, saved, altered, improved, etc.). Providing such notifications, while maintaining protection of sensitive information pertaining to the adjusted record, may prove difficult using conventional systems. This difficulty may be magnified when the user desires that other users receive similar notifications.

SUMMARY

In one example, systems and methods are provided for initiating message listening and routing message content to authorized user devices. In some examples, a notification request is received from a first user device of a first user. The notification request is indicative of a request that one or more second user devices be provided with notifications specifying one or more decisions made or actions performed in relation to responding to current conditions. The current conditions pertain to the first user. In some examples, an authorization request is received from a second user device of the one or more second user devices. The authorization request includes identifying information of the first device or the first user. In some examples, in response to receiving the authorization request, it is determined that the second user device is authorized to receive the notifications specifying the one or more decisions made or actions performed in relation to responding to the current conditions. The determining is based at least in part on verifying at least a portion of the identifying information included in the authorization request. In some examples, one or more listeners are initiated. The one or more listeners are configured to listen for messages on a messaging bus that identify the first user device or the first user. The messages are generated in response to one more events. A portion of the messages are generated by one or more components in network communication with the messaging bus. In some examples, a message is received in response to one of the one or more listeners listening for messages on the messaging bus that identify the first user device or the first user. In some examples, a notification is generated in accordance with one or more notification rules. The notification describes at least one aspect of the message. In some examples, the notification is transmitted to the second user device of the one or more second user devices.

BRIEF DESCRIPTION OF THE DRAWINGS

Various embodiments in accordance with the present disclosure will be described with reference to the drawings, in which.

DETAILED DESCRIPTION

Figure 1:
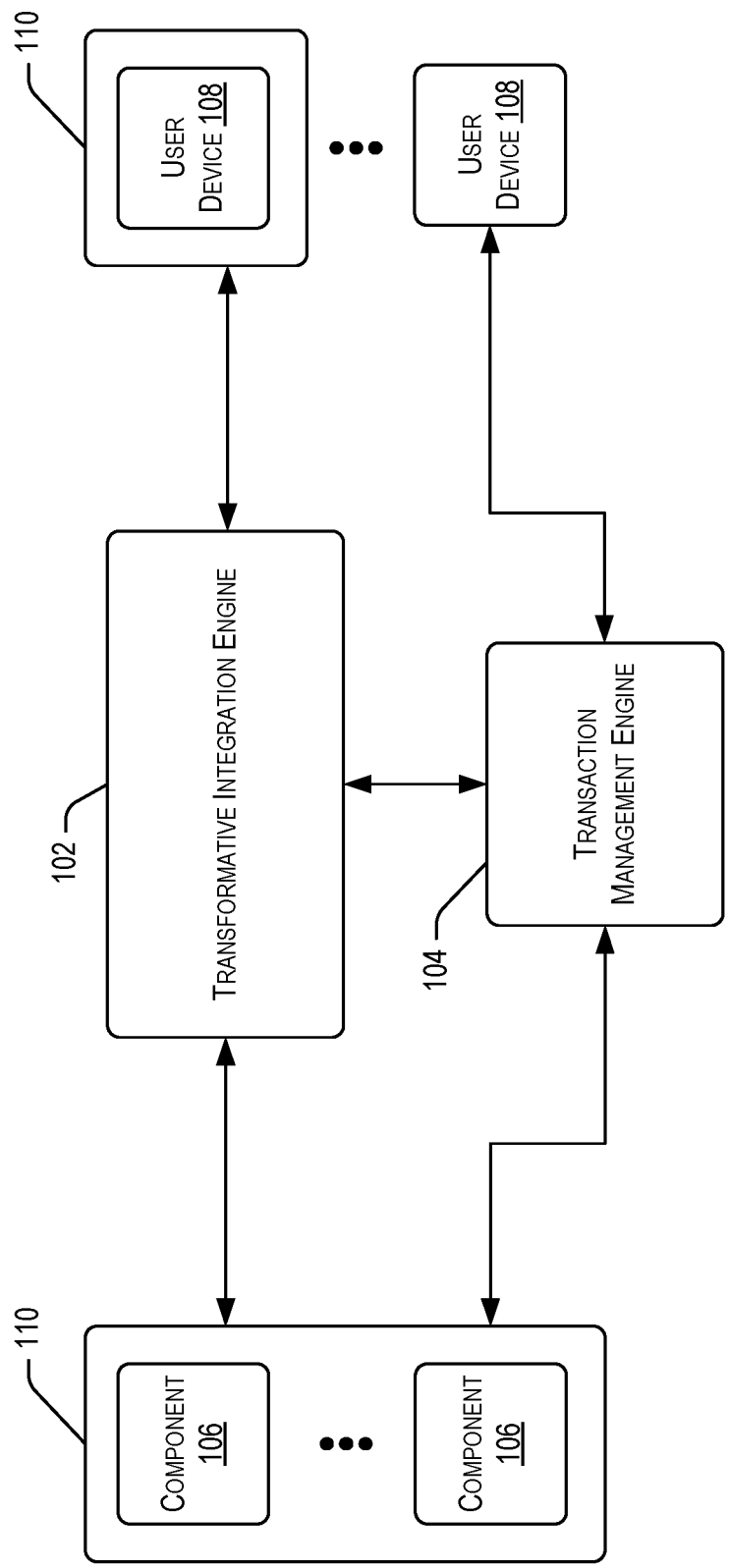
FIG. 1 is an example block diagram illustrating an environment in which techniques relating to initiating message listening and routing message content to authorized user devices as described herein may be implemented, according to at least one example.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In some examples, the present disclosure provides systems and methods to subscribe a member of the public (e.g., a second user) to receive information regarding the treatment of a first user (e.g., a patient). In this example, the first user requests that a notification service provide such messages. To do so, the first user signs up for the notification service at a physical location within a facility (e.g., within a medical care facility), online, or the like and requests that the message service provide notifications to the second user (i.e., indicates that the first user approves of the notification service sending notifications and/or messages to authenticated members of the public). In some examples, this includes providing authorization that text messages be sent to user devices of the first user and the second user, once the second user is authorized. The notification service uses a handshake protocol to authenticate that the second user and the second user device are authorized to receive the notifications, which may include patient care information. In this example, the first user (e.g., patient) is identified by a unique patient identifier (ID), her date of birth, a social security number (e.g., a nine-character government identifier), and other identifying information. In some examples, the second user is a close family member with whom the first user has shared a portion of his or her identifying information or whom the first user has previously authorized to receive text message updates. In this example, the first user identifies an authorized user by sharing a unique code with the particular person. The code is received from the notification service and enables the recipient to become authorized by interacting with the notification service. In some examples, the unique code includes a portion of the identifying information and/or is generated based in part on the identifying information. In other examples, the second user the first user, a medical professional, a family member, or other authorized user. The notification service monitors the flow of messages within a record system (e.g., a medical record system) and keeps the authorized users (e.g., the second user after successful authorization) informed of the first user's process flow (e.g., as the patient progresses through care at a medical care facility) using the text messages. This can include, for example, names of physicians, assigned nurses, assigned rooms, services ordered, when tests are received, medications, commencement of procedures, conclusion of procedures, order for prescriptions, orders for tests, etc. While the notification services does provide status updates in the form of notifications, it includes safeguards to remove protected health information (PHI) from its text message updates.

In some examples, the notification service monitors messages that flow over a common messaging bus to determine messages which are related to the first user. This may include, for example, identifying messages that include the first user's name, unique patient ID, and the like. The messaging bus includes a plurality of virtual pipes (or domains) according to which components and other systems provide messages (e.g., medical messages). For example, when a professional user (e.g., a medical professional such as a doctor, nurse, surgeon, etc., which may be the second user) adds a note to the medical record of the first user at a first computer, the first computer may send the updated note (e.g., a message) to a record service via the messaging bus. The notification service then identifies the updated note as it flows over the messaging bus. In order to identify such messages, the notification service initiates one or more bus listeners which have access to the messaging bus. The one or more bus listeners include software and/or hardware configured to identify certain messages and publish those messages to other systems, entities, and the like. An example bus listener proceeds through one or more authentication steps in order to retrieve messages from off the bus. As part of authentication or otherwise, in this example, the messaging bus includes one or more divisions via hardware, software, or the like to maintain de-identified and identified PHI separate. Such divisions enable the notification service to comply with government regulations relating to the handling of PHI, such as the Health Insurance Portability and Accountability Act (HIPAA). The notification service also includes a look-up table that includes patient identifying information. When a listener identifies a record change, the notification service utilizes the look-up table to match the record change with the first user in order to pull the message corresponding to the first user from the messaging bus. This message may include record information (which may be generic). The message can then be processed (e.g., determine what information should be taken off the bus, translate to a useable format, determine how to transfer it, determine to whom to send it, etc.) and transferred to the end point (e.g., second user device, cell phone, email, twitter feed) associated with the second user and other authorized users.

Once it is determined that a message or a portion of a message should be sent to the second user, a notification may be generated. The notification may be based on the message and in a format capable of being received by a user device of the second user. The notification (or the message or the portion of the message) is provided to a messaging vendor. The messaging vendor may adjust the message prior to sending to the user device of the second user. In some examples, the messaging vendor obtains the notification from the notification service via a virtual private network.

Referring first to FIG. 1, a block diagram of an embodiment of a medical provider network 100 is illustrated. The medical provider network 100 includes a plurality of elements connected with directional arrows. The directional arrows not only indicate that the elements are connected, but also indicate the direction that data may flow with respect to the various elements. For example, data may flow between the following elements of the medical provider network 100: a transformative integration engine 102 and a transaction management engine 104.

Generally, the transformative integration engine 102 is configured to collect and aggregate medical-related data from components of the medical provider network 100 and components outside of the medical provider network 100. Once the transformative integration engine 102 collects and aggregates the medical-related data, it may perform one or more operations with respect to the data and store it in a data store. This stored medical-related data can then be accessed by components within and without the medical provider network 100.

The medical-related data is transmitted throughout the medical provider network 100 in accordance with any suitable transmission protocol. Generally, the transaction management engine 104 is configured to manage the flow of such transmissions within the medical provider network 100. Thus, the transaction management engine 104 receives indications of transmissions of medical-related content and tracks the origination locations of the transmissions, the destination locations of the transmissions, and any locations there between.

The medical provider network 100 includes one or more components 106 and one or more user devices 108. The one or more components 106 are configured to share medical-related data with the transformative integration engine 102, the transaction management engine 104, and each other via one or more communication networks. The one or more user devices 108 are configured to access medical-related data collected by the transformative integration engine 102 and provide their own medical-related data. Users of the one or more user devices 108 may use such medical-related data to help the users make medical decisions. While the one or more components 106 and the one or more user devices 108 are illustrated as communicating via the transformative integration engine 102 and/or the transaction management engine 104, this specification is not so limited. For example, each of the one or more components 106 may communicate with each of the one or more user devices 108 directly via other or the same communication networks. Each of the one or more components 106 of the medical provider network 100 is an example of a device, medical equipment, a lab system, a business terminal, a clinical terminal, or the like that can receive and/or provide medical-related data as further detailed herein. Each of the one or more user devices 108 is an example of a user device that can receive and/or provide medical-related data as further detailed herein. In some examples, at least some of the one or more user devices 108 may function similar to at least some of the one or more components 106 and vice-versa. In other words, each of the one or more user devices 108 and each of the one or more components 106 may both provide data and access data within the medical provider network 100.

In some examples, the one or more components 106 are each associated with one or more medical provider organizations within the same or different medical provider networks. For example, certain ones of the one or more components 106 may be associated with a first medical provider organization, while other ones of the one or more components 106 may be associated with a second medical provider organization. Additionally, each of the one or more components 106 may be associated with a medical care facility 110. The medical care facility 110 illustrates an example of one medical care facility. The medical provider network 100, however, may include many different types of medical care facilities (e.g., urgent care facilities, outpatient facilities, hospitals, clinics, and medical record service facilities) including many different types of components. In some examples, the one or more components 106 are not associated with one of the medical care facilities 110, but instead are included as part of an information systems company that manages medical-related data such as electronic medical records.

The one or more components 106, irrespective of which medical provider organization each belongs to, may be capable of receiving, generating, processing and/or transmitting medical-related data. Examples of the one or more components 106 include, for example, a user device (e.g., computer, mobile device, smart phone, laptop, electronic badge, set-top box, thin client device, tablet, pager, and other similar user devices), clinical lab equipment (e.g., fluid processing device, chemistry analysis device, coagulation analysis device, DNA analysis device, genetic analysis device, urinalysis device, hematology analysis device, immunology analysis device, and other similar lab equipment), medical equipment (e.g., surgery tools, imaging machines, and other similar medical devices), business and/or administrative device that can receive input from (for example) a nurse, administrator, receptionist, secretary or assistant (e.g. server, computer, mobile device, smart phone, laptop, electronic badge, set-top box, thin client device and other similar business and/or administrative devices), and other similar devices capable of generating medical-related data. The one or more components 106 also includes entities that collect, aggregate, and store medical-related data. Some of these entities may be third-parties that make medical-related data available to the transformative integration engine 102.

The one or more components 106 provide medical-related data using one or more formats, some of which can be proprietary. For example, a magnetic resonance imaging (MRI) machine (e.g., one of the one or more components 106) manufactured by company A, located within a first medical care facility (e.g., the medical care facility 110), and belonging to a first medical provider organization, may save and transfer data in a first format. An MRI machine (e.g., one of the one or more components 106) manufactured by company B, located within the first medical care facility (e.g., the medical care facility 110), and belonging to the first medical care provider, may save and transfer data in a second format. In some examples, medical-related data from certain components is transformed, translated, or otherwise adjusted to be recognizable by the transformative integration engine 102. Thus, continuing with the example from above, when the Mill machines manufactured by companies A and B are located within the first medical care facility belonging to the first medical care provider, they may nevertheless save and transfer data in different formats. In some examples, the one or more components 106 communicate using the Health Level-7 (HL7) standard for hospital information systems or any other suitable format.

The transmission of medical-related data from the one or more components 106 to the transformative integration engine 102 may be triggered by a variety of different events. For example, the medical-related data may be transmitted periodically, upon detection of an event (e.g., completion of an analysis or end of a procedure), upon detection of an event defined by a rule (e.g., a user-defined rule), upon receiving user input triggering the transmission, or upon receiving a data request from the transformative integration engine 102. Each transmission can include, e.g., a single record pertaining to a single patient, procedure, or analysis or multiple records pertaining to multiple patients, procedures, or analyses.

In some examples, at least some of the one or more user devices 108 are associated with the medical care facility 110.

At least some of the one or more user devices 108 may not be associated with the medical care facility 110 or any other medical care facility. Similar to the one or more components 106, the one or more user devices 108 may be capable of receiving, generating, processing and/or transmitting medical-related data. Examples of the one or more user devices 108 include, for example, a computer, a mobile device, a smart phone, a laptop, an electronic badge, a set-top box, a thin client device, a tablet, a pager, and other similar user devices). The one or more user devices 108 may differ from the one or more components 106 because the one or more user devices 108 may be configured to run one or more applications developed for interacting with the medical-related data collected by the transformative integration engine 102. For example, those user devices of the one or more user devices 108 that are not associated with the medical care facility 110 may be configured to run one or more third-party applications that may rely in part on the medical-related data gathered by the transformative integration engine 102.

Each of the one or more components 106 and the one or more user devices 108 may be utilized by one or more users (not shown). Each of the one or more users may be associated with one or more medical provider organizations. For example, one of the one or more users can be associated with a medical provider organization as a result of being employed by the organization, physically located at a location of the organization, being an agent of the organization or receiving a medical service from the organization.

The connections between the one or more components 106 and the one or more user devices 108 and the transformative integration engine 102 and the transaction management engine 104 are illustrated by a plurality of bi-directional arrows indicating that medical-related data may flow therebetween. The medical-related data flows in either direction within the medical provider network 100 (e.g., from the transformative integration engine 102 and the transaction management engine 104 towards the one or more components 106 and/or the one or more user devices 108 or to the transformative integration engine 102 and the transaction management engine 104 from the one or more components 106 and/or the one or more user devices 108). The connections between the one or more components 106 and the one or more user devices 108 and the transformative integration engine 102 and the transaction management engine 104 can include any suitable network connection. A connection can be configured to support communication over a wireless medium, e.g., using Wi-Fi (IEEE 802.11 family standards), Zigbee, Bluetooth® (a family of standards promulgated by Bluetooth SIG, Inc.), Bluetooth Low Energy or other protocols for wireless data communication. In some instances, a connection can include a wired connection.

In some examples, the one or more components 106 and the one or more user devices 108 may communicate with the transformative integration engine 102 and the transaction management engine 104 via different information formats, different proprietary protocols, different encryption techniques, different languages, different machine languages, and the like. As will be discussed with reference to FIG. 2, the transformative integration engine 102 is configured to receive these many different communications from the one or more components 106, and in some examples from the one or more user devices 108, in their native formats and transform them into any of one or more formats. The received and/or transformed communications can be transmitted to one or more other devices (e.g., the transaction management engine 104, an entity device and/or a user device) and/or locally or remotely stored. In some examples, the transformative integration engine 102 receives medical-related data in the HL7 format or conforming to any other suitable format and/or is configured to transform received data to conform with the HL7 format.

In some examples, the medical provider network 100 may not include the transformative integration engine 102, or may include part of the functionality described herein. For example, when the communications between the one or more user devices 108 and between the one or more components 106 are in the same format, the transformative integration engine 102 may not be required to transform the communications into other formats.

As used herein, medical-related data can include, for example, health information that is created or received by a health care provider, a processed or unprocessed version of medical data detected by medical equipment, and/or user-identified data. Medical-related data can include information that identifies a patient, such as personal information and/or demographic information. For example, the information can identify a patient's name, age, sex, race, physical address, phone number, email address and/or social security number. Medical-related data may include information collected by a health plan, a public health authority, an employer, a life insurer, a school or university, or a health care clearinghouse that relates to the past, present, or future physical or mental health or condition of any individual.

Medical-related data can include financial and/or insurance information corresponding to the patient. For example, the information can identify an insurance company, insurance plan, member identification number, group number, insurance contact information (e.g., address and/or phone number), deductible information, out-of-pocket information, copay information, an employer, an occupation and/or salary information.

Medical-related data can include medical-history information, such as past diagnoses, past or present symptoms or past procedures and/or corresponding dates (e.g., of diagnoses, symptom initiations and/or procedures). Medical-related data can identify past or present medications being taken by or having been prescribed to the patient and corresponding dates. In some examples, the medical-related data can identify orders pharmacology orders, whether associated with a patient, doctor, or otherwise.

Medical-related data can include an identification of one or more medical services having been, being or having been requested by a patient. A medical service can include, for example, an evaluation performed by a medical care professional, a medical test, a surgery and/or other procedure. Medical-related data can identify a medical test or analysis that was performed or prescribed and/or a result of the test or analysis. For example, information can indicate that a test (e.g., lab test, Mill, x-ray, CT scan, echocardiography, EKG, EEG, EMG, or ultrasound) was performed on a particular date and/or by a particular entity and can further include a processed and/or unprocessed result of the test (e.g., a count or level; an indication as to whether a test result is normal; and/or an indication as to whether a particular feature (e.g., a fracture, tumor, lesion, slowed nerve conduction) was observed and/or a magnitude of the feature). Medical-related data can include any information pertaining to genes of generic populations, patients, sets of patients, living organisms, and of any other suitable group. Information pertaining to genes includes, for example, genomic information (e.g., DNA sequencing), hereditary information, classical genetic information, molecular genetic information, any other suitable information pertaining to genes.

Medical-related data can identify one or more care providers or institutions. The care provider and/or institution can be one associated with recent or past care and/or with the patient. For example, data can be transmitted for a patient admitted in Hospital A and being treated by Specialist B, though the data can also identify that the patient's primary care physician is Doctor C.

Medical-related data may, or may not, selectively pertain to a particular patient. For example, non-patient-specific data may include a price of a prescription, a recommended or approved dosing schedule for a medication, a work schedule for a physician, an acceptance criteria for a clinical study, non-patient-specific data can include information pertaining to the operation of a medical care facility, financial information, administrative information, and generic clinical information.

Medical-related data can, depending on the implementation, include individually identifiable health information and/or de-identified information. Individually identifiable health information includes, for example, health information, including demographic information collected from an individual that is created or received by a health care provider, health plan, employer, or health care clearinghouse; and that relates to the past, present, or future physical or mental health or condition of an individual, the provision of health care to an individual, or the past, present, or future payment for the provision of health care to an individual; and that identifies the individual; or, with respect to which there is a reasonable basis to believe, can be used to identify the individual. De-identified information includes information that cannot be used on its own or with other information to identify a person to whom the information belongs.

As used herein, medical-related data can include protected health information, which can include individually identifiable health information that is transmitted by electronic media, maintained in electronic media, or transmitted or maintained in any other form or medium. Examples of protected health information, include, for example any information about health status, provision of health care, or payment that can be linked to a particular patient and may include any of the following information capable of identifying the patient: names, geographic identifiers, dates directly relating to the patient, phone numbers, fax numbers, email addresses, social security numbers, medical record numbers, health insurance beneficiary numbers, account numbers, certificate/license numbers, vehicle identifiers and serial numbers, device identifiers and serial numbers, web Uniform Resource Locators, Internet Protocol addresses, biometric identifiers (e.g., finger, retinal, and voice prints), full face photographic images and any comparable images, and any other unique identifying number, characteristic, or code.

The one or more components 106 of the medical care facility 110 can include and/or has access to a local or remote memory for storing generated medical-related data. In some examples, the medical-related data is stored by one or more servers local to the medical care facility 110. Such storage may enable the medical care facility 110 to retain locally medical-related data pertaining to its own patients prior to (or in conjunction with) the medical-related data being shared with the transformative integration engine 102 and/or the transaction management engine 104. In some examples, the one or more servers of the medical care facility 110 share medical-related data directly with a record service (not shown), and the record service makes the medical-related data available to the transformative integration engine 102 and/or the transaction management engine 104. Once an electronic medical record is updated at the medical care facility 110, an indication of the update may be provide to the record service. The record service may then update a corresponding record associated with the electronic medical record.

The record service can be granted access to the medical-related data generated and/or transmitted by the one or more components 106. In some examples, the record service includes a server or a plurality of servers arranged in a cluster or the like. These server(s) of the record service can process and/or store medical-related data generated by the one or more components 106. For example, one or more records can be generated for each patient (e.g., each record corresponding to a different entity or being shared across entities). Upon receiving a communication with medical-related data from an component (or medical care facility), the record service can identify a corresponding record and update the record to include the medical-related data (or processed version thereof). In some examples, the record service provides medical-related data to the transformative integration engine 102.

The medical care facility 110 is a facility at which care is provided to patients. Irrespective of the type of medical care facility, the medical care facility 110 may treat patients, update medical-related data, maintain medical-related data, and communicate medical-related data to the transformative integration engine 102. At least some of the medical-related data may be stored local to the medical care facility 110. Further, the one or more components 106 within the medical care facility can generate medical-related data including administrative information, clinical information, and financial information as part their operations within the urgent care facility. Examples of medical care facilities include, for example, urgent care facilities, outpatient facilities, hospitals, clinics, and other suitable facilities at which care is provided to patients.

The medical care facility 110 can be an urgent care facility, an insta-care facility, an emergency room, or the like. For example, a doctor may update a particular electronic medical record of a patient using one of the one or more components 106 or one of the one or more user devices 108 after receiving the patient in the course of an emergency. In some examples, the urgent care facility may be distinct from an office of the patient's primary care provider. However, in accordance with techniques described herein, the updates to the electronic medical record may be made available to the patient's primary care provider, including any medical-care professionals. The update can also be saved locally in association with the patient's electronic medical record, a copy (or the original) can be provided to the transformative integration engine 102, and an indication of the update can be provided to the transaction management engine 104. In some examples, the indication of the update is generated by the transaction management engine 104 as the update is provided to the transformative integration engine 102.

The medical care facility 110 can be an outpatient facility (e.g., a long-term care facility, a recovery facility, a hospice facility, a rehabilitation center, a retirement home, or the like). Such a facility may In some examples, the outpatient facility provide medical care to patients who are not admitted to a hospital. Additionally, components within the outpatient facility generate medical-related data (e.g., administrative information, clinical information, and financial information) as part their operations within the outpatient facility. For example, an outpatient facility may provide treatment to a patient using a dialysis machine. Information pertaining to the treatment of the patient using the dialysis machine can be stored locally, and a copy can then be provided to the transformative integration engine 102 such that it can coordinate storage and later retrieval of the information for use by one or more others of the one or more components 106 of the one or more user devices 108. In addition, an indication of the update to the medical-related data is provided to the transaction management engine 104 (e.g., directly or via transformative integration engine 102). The record service can also maintain updated medical-related data including electronic health record information from the outpatient facility.

The medical care facility 110 can be a hospital (e.g., a type of medical care facility that provides medical, surgical, and other types of medical and nursing care). In this example, the hospital includes one or more different wards dedicated to the care and treatment of patients with particular diseases, disorders, and the like. Within the wards, the hospital includes a variety of different components capable of generating medical-related data. The hospital can store a portion of the generated medical-related data for its own patients locally. In some examples, users (e.g., patients, doctors, etc.) may utilize the one or more components 106 and/or the one or more user devices 108 to generate such medical-related data. For example, the hospital may include, as one of its components, an MRI machine. A technician (e.g., a user) may collect one or more MRI images of a patient using the MRI machine at the hospital. These MRI images, a form of medical-related data, can be stored locally, and a copy of the file can be provided to the transformative integration engine 102, which can coordinate storage and later retrieval of the information for use by one or more others of the one or more components 106 of the one or more user devices 108.

In addition, an indication of the medical-related data can be directly or indirectly provided to the transaction management engine 104. Components of the hospital can also or alternatively communicate the medical-related data to the transformative integration engine 102 or the record service. In this manner, the transformative integration engine 102 has access to updated medical-related data for the patients of the hospital.

The medical care facility 110 can be a clinic (e.g., an organization of medical care professionals that provide routine medical care). In this example, the treatment offered by the clinic is devoted primarily to outpatients. The clinic offers medical services options to populations in local communities and, in some examples, provides medical services to patients prior to the hospital providing medical services.

The medical provider network 100 includes the one or more components 106 and the one or more user devices 108. One or more users (not shown) can access the components 106 and the user devices 108 to generate, provide, and access medical-related data within the medical provider network 100. In some examples, the medical-related data may have been received by the transformative integration engine 102 and retained for use by others of the components 106 and/or the user devices 108. The one or more users can include, for example, first responders, medical care professionals, patients, or any other suitable type of user.

The first responder can include, for example, an emergency medical technician, a firefighter, a police officer, a member of the military, a designated medical volunteer, and the like. In the context of this specification, the first responder is typically dispatched or directed to the scene of an accident in order to provide medical support to victims.

In some examples, the first responder provides medical-related data to the transformative integration engine 102 using one of the one or more user devices 108 as part of responding to the dispatch. For example, in one example, the first responder arrives at a car accident, identifies a victim by one more means of identification (e.g., a driver's license number, name, address, etc.), and shares the identifying information with the transformative integration engine 102 via one of the one or more user devices 108 (e.g., a mobile phone, a radio, or other communication device). In return, the transformative integration engine 102 can facilitate the provision of medical-related data associated with the victim to the first responder. In this manner, the first responder can be informed of, for example, the medical history and other considerations while providing medical treatment to the victim.

The first responder can provide and/or receive the medical-related data via the one or more user devices 108. Thus, at least in this example, the one or more user devices 108 may operate according to a private and/or proprietary network or protocols. In other examples, the one or more user devices 108 may operate on public networks. In any case, however, the transformative integration engine 102 can have access to the one or more components and can communicate with them via a public, private and/or proprietary network or protocols. The use of one or more private and/or proprietary protocols can promote secure transfer of medical-related data.

In some examples, the one or more users can include a medical care professional and/or care provider. The medical care professional and/or care provider can provide one or more medical-related services, including, for example, examination, surgery, diagnosis, consultation, counseling, scheduling of visits, handling of protected health record information, payment handling, coordination of care, management of care, and the like. In some examples, the medical care professional is associated with the medical care facility 110. In some examples, the medical care professional is a doctor, a nurse, a surgeon, a physical therapist, a medical assistant, a facility staff person, an administrative employee, or any other person who utilizes medical-related data for treatment of patients. In this example, the medical care professional utilizes some of the one or more user devices 108 to send medical-related data to, and/or receive from, the transformative integration engine 102, medical-related data. In this manner, the medical care professional can receive updates, statuses, progress, and the like relating to patients of the.

In some examples, the one or more users can include a patient. The patient can be a patient of the medical care facility 110, the first responder, and/or the medical care professional. The patient can include one that has expressly or implicitly authorized the medical care facility 110, the first responder and/or the medical care professional to access and record medical-related data pertaining to services provided to the patient.

Figure 2:
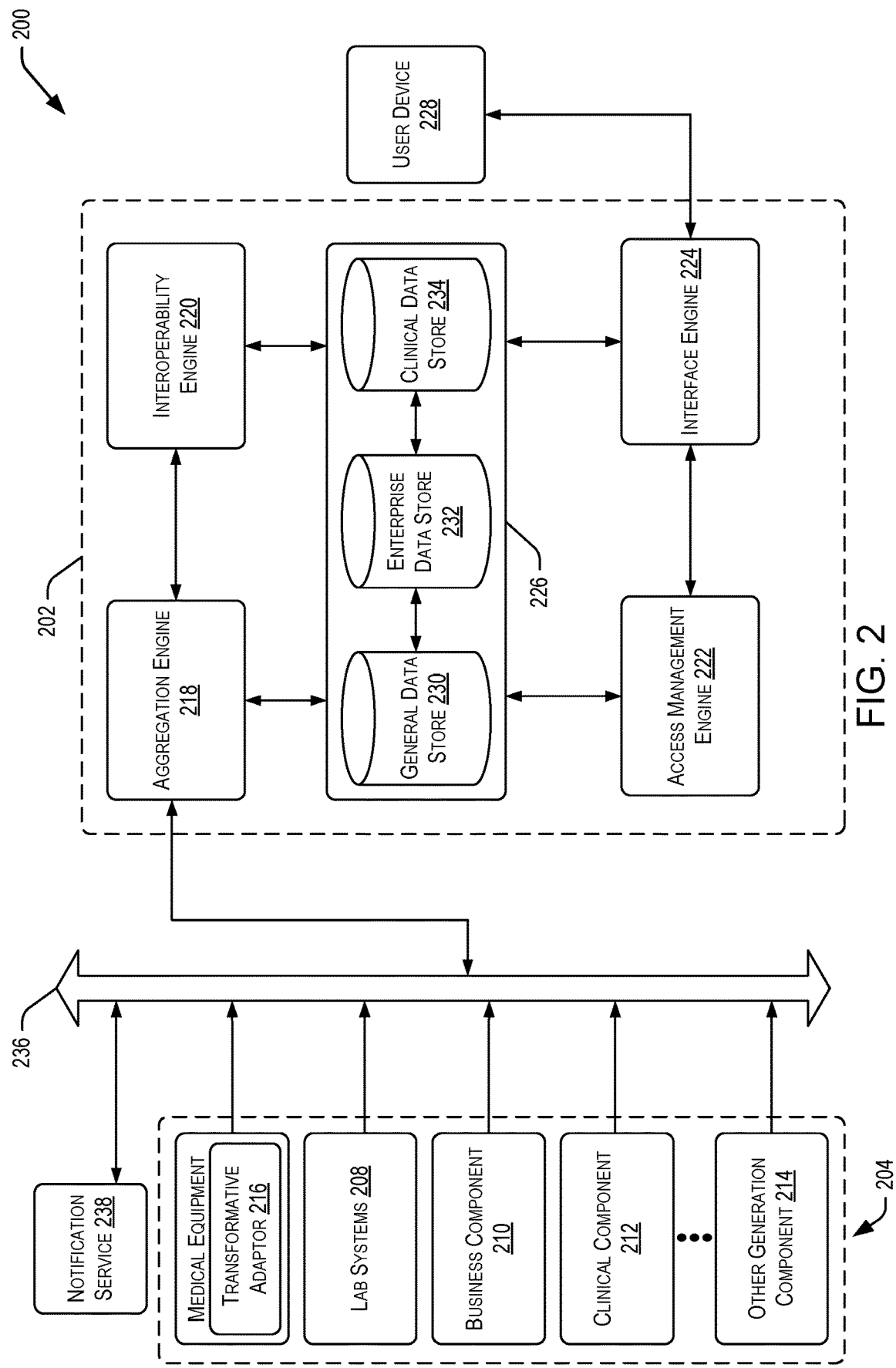
FIG. 2 is an example block diagram illustrating an environment in which techniques relating to initiating message listening and routing message content to authorized user devices as described herein may be implemented, according to at least one example.

Referring next to FIG. 2, a block diagram of an example of a medical provider network 200 is shown. The medical provider network 200 includes a transformative integration engine 202. The transformative integration engine 202 is an example of the transformative integration engine 102 discussed with reference to FIG. 1. The medical provider network 200 also includes one or more generation components 204. In particular, the one or more generation components 204 includes a medical equipment component 206, a lab systems component 208, a business component 210, a clinical component 212, and other generation component 214. The one or more generation components 204 are examples of the one or more components 106 discussed with reference to FIG. 1. The one or more generation components 204 are configured to provide medical-related data to the transformative integration engine 202. In some examples, the medical-related data may pass to the transformative integration engine 202 via a messaging hub 236. In some examples, only a portion of the medical-related data is passed via the messaging hub 236, while other portions are passed directly to the transformative integration engine 202 without first passing over the messaging hub 236.

Generally, the one or more generation components 204 includes any suitable device or system capable of generating medical-related data in the context of a medical provider network. For example, the other generation component 214 may include a sensor on a door in a hospital, and the medical equipment component 206 may include a sophisticated computer-controlled laser surgery device. In either case, each generation component generates some type of medical-related data. For example, the medical-related data provided by the sensor may be used to address security concerns or assessing heating, ventilating, and air conditioning (HVAC) costs for the hospital. The medical-related data provided by the laser surgery device may have been provided while operating on a patient and may then be used by other doctors in the future to decide how to use the device on their own patients.

As discussed in further detail herein, medical-related data generated by the one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical medical provider network includes thousands of generation components producing data in hundreds of formats. In order to harness the power that comes from such a large amount of medical-related data to make informed health care decisions, it is desirable that all, or at least a large portion of the data, is shared. Use of the transformative integration engine 202 in accordance with techniques described herein may achieve this design—making large amounts of data, in many different originating format, available to doctors, nurses, patients, administrators, and third parties, via one or more interfaces.

While the one or more generation components 204 are illustrated adjacent to each other, it is understood that each may be located within one facility or that the components may be spread out among many facilities. In addition, in some examples, the one or more generation components 204 belong to different medical provider organizations.

Turning now to the medical equipment component 206, this component includes any medical machine, contrivance, implant, or other similar related article, that is intended to aid in the diagnosis, monitoring, or treatment of medical conditions. This includes, for example, diagnostic equipment, including medical imaging machines (e.g., ultrasound machines, magnetic resonance imaging (MRI) machines, positron emission tomography (PET) scanners, computed tomography (CT) scanners, and x-ray machines); therapeutic equipment (e.g., infusion pumps, medical lasers, and laser-assisted in situ Keratomileusis (LASIK) lasers); life support equipment (e.g., medical ventilators, anesthetic machines, heart-lung machines, extracorporeal membrane oxygenation (ECMO) machines, and dialysis machines) and/or medical monitors to measure patient's medical state (e.g., electrocardiography (ECG), electroencephalography (EEG), blood pressure machines, and equipment for monitoring dissolved gases in the blood). Each of the above-listed components generates medical-related data that is provided to the transformative integration engine 202.

As illustrated, the medical equipment component 206 includes transformative adaptor 216. In some examples, the transformative adaptor 216 is a device that transforms, translates, converts, or otherwise adjusts output data from the medical equipment component 206. For example, a medical equipment component 206 can be a CT scanner that outputs its results in format A, but the majority of other CT scanners in the medical provider network output their results in format B. The transformative adaptor 216 may be implemented to convert or otherwise adjust the results in format A to conform closer to format B. For example, the conversion from format A to format B may be performed using a conversion rule, which may be user-define or learned. The transformative integration engine 202 may perform similar tasks as it relates to all data generated within the medical provider network 200. In this manner, the transformative adaptor 216 can perform an initial step in the process of transformation, translation, conversion, or adjustment of the output of the medical equipment component 206. In some examples, the transformative adaptor 216 is implemented in hardware, software, or any suitable combination of both. In some examples, other transformative adaptors (not shown) may be implemented within others of the one or more generation components 204. In some examples, the medical equipment component 206 may not include the transformative adaptor 216.

The lab systems component 208 includes any suitable medical laboratory equipment or system that is intended to analyze material related to patient care. This includes, for example, medical laboratory equipment that analyzes blood, urine, and genes; electric microscopes; ultracentrifuges; data collection devices, including Kymographs, sensors connected to a computer to collect data; monitoring devices; computers used by clinicians to report results of lab tests, and other similar medical laboratory equipment. Each of the above-listed components generates medical-related data that is provided (directly or indirectly) to the transformative integration engine 202. The provided data can further include an identification of a patient and/or other patient-pertinent information (e.g., actual or suspected diagnosis and/or demographic information).

The business component 210 includes any suitable computing devices used for business-related purposes with respect to the medical provider network 200. For example, the business component 210 can be configured to receive inputs by employees of a hospital to prepare medical-related data including business-related data relating to eligibility and registration of patients, scheduling and throughputs, general supply chain materials management, pharmacy supply chain materials management, human resources, financial documentation and logging, building operations, information technology systems, marketing, budgeting, and other similar business-related purposes. In some examples, the business-related information is auto-generated or populated by the business component 210. At least a portion of such information is provided to the transformative integration engine 202.

The clinical component 212 includes any suitable computing device used in research, treatment, and care of patients. For example, the clinical component 212 is used to generate medical-related data including clinical data, which may further include an identification of a patient and/or other patient-pertinent information. For example, the clinical component 212 is used by nurses, technicians, doctors, and/or other individuals associated with a hospital, clinic, lab, or other similar entity to prepare clinical data. Clinical data includes, for example, output relating to computerized physician order entry (CPOE), protected health information for patients (i.e., a subset of medical-related data), dictations, lab results, lab requests, lab tests, orders for medical supplies, intake and checkout of patients, medical reports, clinical tests, clinical documentation, and other similar clinical information. At least a portion of such information is provided to the transformative integration engine 202. In some examples, the clinical data is auto-generated or populated by the clinical component 212. The clinical component 212 and the business component 210 are often selected from a similar group of computing devices.

As described herein, a notification service 238 shares a network connection with the messaging hub 236. The notification service 238 is configured to monitor medical-related data (e.g., medical messages) that is passed over the messaging hub 236 and, from the monitored data, select certain portions to provide to one or more authorized users (e.g., patients, friends and family members of patients, medical care professionals, and other suitable authorized users).

Each of the one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting medical-related data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with the transformative integration engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or the transformative integration engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive medical-related data from one or more sensors. For example, a particular port may include an interface for receiving data collected from an ultrasound machine. The sensors may be any suitable type of sensor to capture data. Such captured data may be shared with the transformative integration engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the medical-related data provided by the component or the user device located at the geographic location.

The transformative integration engine 202 includes an aggregation engine 218, an interoperability engine 220, an access management engine 222, an interface engine 224, and a data store 226. Generally the aggregation engine 218 is configured to collect medical-related data of different formats generated by the one or more generation components 204. The aggregation engine 218 may also be configured to perform one or more operations on the collected data. For example, the aggregation engine 218 may tag data, log data, perform protocol conversion, and may support one-to-many communications. The collection may be asynchronous. In some examples, the medical-related data has been saved locally in connection with the one or more generation components 204 in many different formats having many different data structures.

The aggregation engine 218 is configured to receive such diverse (or, in other embodiments, uniformly formatted) data and provide it to the interoperability engine 220. The interoperability engine 220 is configured to perform one or more operations on the received medical-related data and store it in the data store 226. For example, the interoperability engine 220 may perform semantic tagging and indexing of medical-related data. This may include extracting field values from data, categorizing data (e.g., by type of data, characteristic of patient, location of medical care facility, characteristic of medical care facility, and the like), anonymizing or partially-anonymizing data, and the like. The interoperability engine 220 may also include a high availability cache, an alerts engine and a rules engine. In some examples, the interoperability engine 220 operates synchronously.

From the interoperability engine 220, medical-related data flows to the data store 226. The data store 226 (and any other data store discussed herein) may include one or more data stores, which may be distributed throughout two or more different locations (e.g., present on different devices, which can include devices of different entities and/or a cloud server). In some examples, the data store 226 includes a general data store 230, an enterprise data store 232, and a clinical data store 234. Within each of the data stores 230, 232, and 234 is stored medical-related data. Depending on the structure of the particular data store, certain data stores may include rules for reading and writing. The data stores 230, 232, and 234 may include records, tables, arrays, and the like, which may be relational or non-relational. Depending on the data store, records for individual patients, results of clinical studies, business and analytics information, output data from the one or more generation components 204, and the like may be retained. The data within the data stores 230, 232, and 234 include elements or tags such that a particular data (e.g., for a single patient, doctor, diagnosis, type of doctor, type of treatment, patients matching a criteria, and the like) can be retrieved.

The access management engine 222 is configured to manage access to features of transformative integration engine 202, including access to the medical-related data retained in the data store 226. For example, the access management engine 222 may verify that a user device such as user device 228 is authorized to access the data store 226. To verify the user device 228, the access management engine 222 may require that a user of the user device 228 input a username and password, have a profile associated with the medical provider network, have paid a subscription fee associated with access to the data store 226, and the like. The access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

The interface engine 224 is configured to retrieve the data from the data store 226 and provide one or more interfaces for interacting with elements of the transformative integration engine 202. For example, the interface engine 224 includes an interface by which an application running on user device 228 can access portions of data within the data store 226

Figure 3:
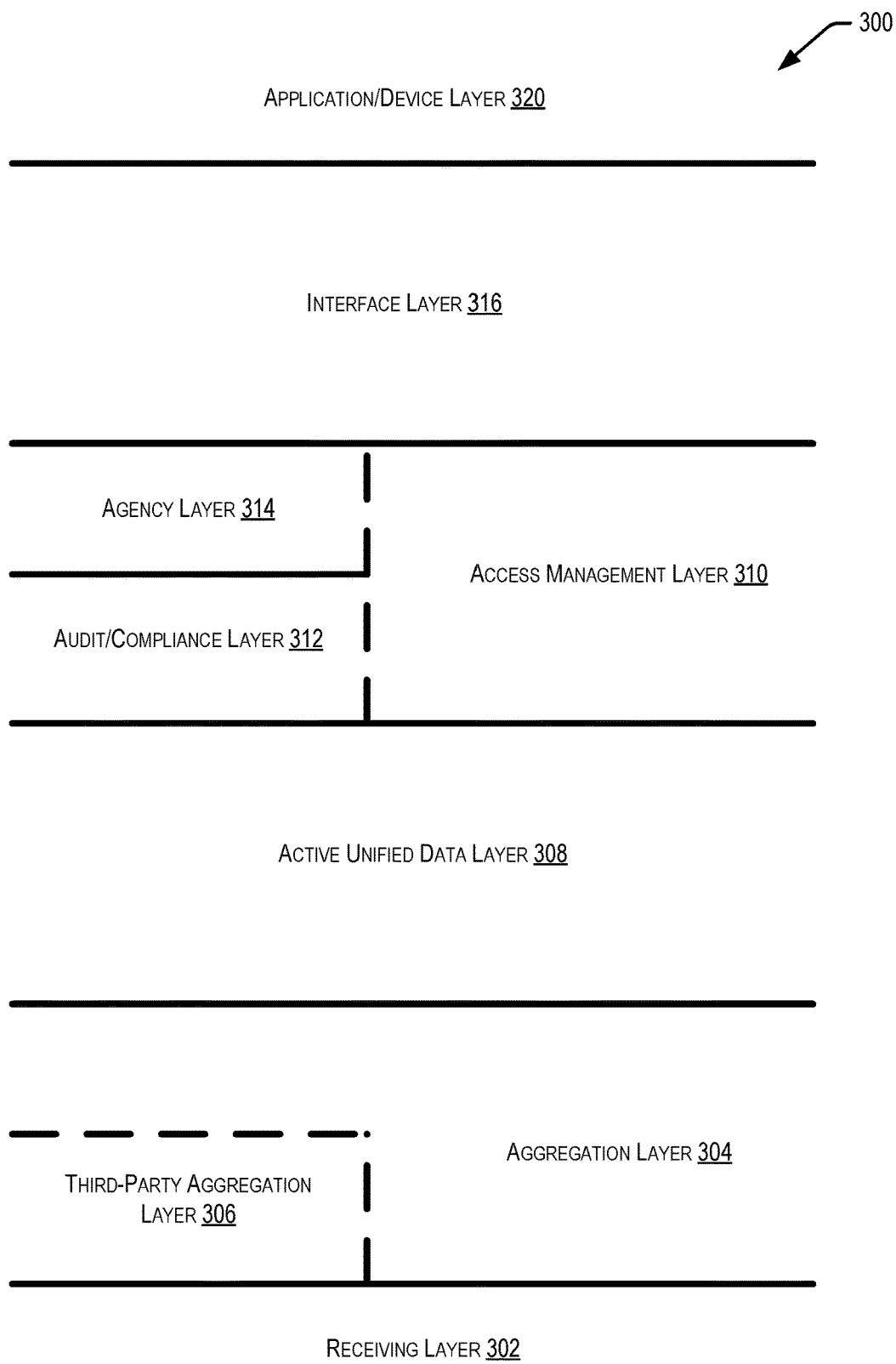
FIG. 3 is an example schematic model illustrating an a network communication model in which techniques relating to initiating message listening and routing message content to authorized user devices as described herein may be implemented, according to at least one example.

Turning next to FIG. 3, a medical architecture stack 300 is shown. In some examples, techniques relating management of medical-related data are implemented in accordance with the medical architecture stack 300. And while the medical architecture stack 300 is illustrated as having a particular structure, it is understood that other structures, including those with more or less layers than illustrated, is within the scope of this specification. In some examples, the medical architecture stack 300 is implemented across a medical provider network having a plurality of systems belonging to the same medical provider organization or spread across different medical provider organizations. Thus, the medical architecture stack 300 can be used to integrate different systems of different organizations, entities, and the like and to provide a fluid sharing of information among elements within the medical provider network and without the medical provider network. In some instances, a multi-layer part of the medical architecture stack 300 is implemented at a single system or device within a medical provider network.

The different layers of the medical architecture stack 300 will be described generally with reference to FIG. 3 and in detail with reference to subsequent figures. The medical architecture stack 300 includes a receiving layer 302 as the bottom-most layer. The receiving layer 302 includes receiving medical-related data from elements that share medical-related data with other elements within an aggregation layer 304. For example, as detailed herein, the receiving layer 302 can include receiving medical-related data from generation components that generate medical-related data. As such, the receiving layer 302 is where medical-related data that has been created is received. In some examples, the data within the receiving layer 302 may be in its raw formats. For example, output from an MRI machine may be received within the receiving layer 302. The output may then be transmitted to the aggregation layer 304. In some examples, components of the receiving layer 302 may have complimentary layers to facilitate data transfer. For example, the components may include a data generation and/or a data transmission layer for providing data to the receiving layer 302.

Elements of the aggregation layer 304 aggregate the medical-related data generated by the elements of the receiving layer 302. For example, the elements of the aggregation layer 304 may include aggregation engines that collect data from generation components located within the receiving layer 302. Such aggregation may be performed periodically, in response to a user request, according to a schedule, or in any other suitable manner. In some examples, data of the aggregation layer 304 may be aggregated according to input and/or rules and may aggregate across records pertaining to, e.g., a same medical care professional, medical care facility, entity, time period, patient characteristic (e.g., demographic characteristic or condition), patient health outcome, and any other suitable input and/or rules. Exemplary data being aggregated can include, e.g., diagnosis for particular patients and/or patient groups, test results, treatment parameters or characteristics, health outcomes (e.g., side effect occurrence, mortality, readmissions, sepsis, etc.), pharmacy orders, patient record data, and the like. The aggregation may include compiling the data, generating a distribution, generating a statistic pertaining to the data (e.g., average, median, extremum or variance), converting the data, transforming the data to different formats, and the like.

Next, the medical architecture stack 300 includes an active unified data layer 308. Elements of the active unified data layer 308 receive medical-related data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of the active unified data layer 308 may receive information collected or generated within the aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within the active unified data layer 308.

The medical architecture stack 300 also includes an access management layer 310, which can include an audit/compliance layer 312 and/or an agency layer 314. The access management layer 310 includes elements to manage access to the medical-related data. For example, the access management layer 310 may include elements to verify user login credentials, IP addresses associated with a user device, and the like prior to granting the user access to data stored within the active unified data layer 308.

The audit/compliance layer 312 includes elements to audit other elements of the medical architecture stack 300 and ensure compliance with operating procedures. For example, this may include tracking and monitoring the other elements of the access management layer 310.

The agency layer 314 includes an access location (e.g., a virtual private network, a data feed, or the like) for elements of agencies that are interested in the operations of the medical provider network in which the medical architecture stack 300 is implemented. For example, the agency layer 314 may allow a governmental entity access to some elements within the medical architecture stack 300. This may be achieved by providing the governmental entity a direct conduit (perhaps by a virtual private network) to the elements of the access management layer 310 and the medical-related data within the active unified data layer 308. The audit/compliance layer 312 and the agency layer 314 are sub-layers of the access management layer 310.

The medical architecture stack 300 also includes interface layer 316. The interface layer 316 provides interfaces for users to interact with the other elements of the medical architecture stack 300. For example, medical care providers, patients, medical care administrators, and others belonging to the medical provider network may utilize one or more user devices (interacting within the application/device layer 320) to access the medical-related data stored within the active unified data layer 308. In some examples, the users may be unrelated to the medical provider network (e.g., ordinary users who are not patients, family members of patients, research universities, for profit and non-profit research organizations, world health care organizations, disaster relief organizations, and the like) and may use applications (not shown) to access the elements within the medical architecture stack 300 via one or more interfaces (e.g., to access medical-related data stored within the active unified data layer 308). Such applications may have been developed by the medical provider network or by third-parties Finally, the medical architecture stack 300 includes application/device layer 320. The application/device layer 320 includes user devices and applications for interacting with the other elements of the medical architecture stack 300 via the elements of the interface layer 316. For example, the applications may be web-based applications, patient portals, doctor portals, mobile applications, widgets, and the like for accessing the medical-related data. These applications may run on one or more user devices. The user devices may be any suitable user device as detailed herein.

Figure 4:
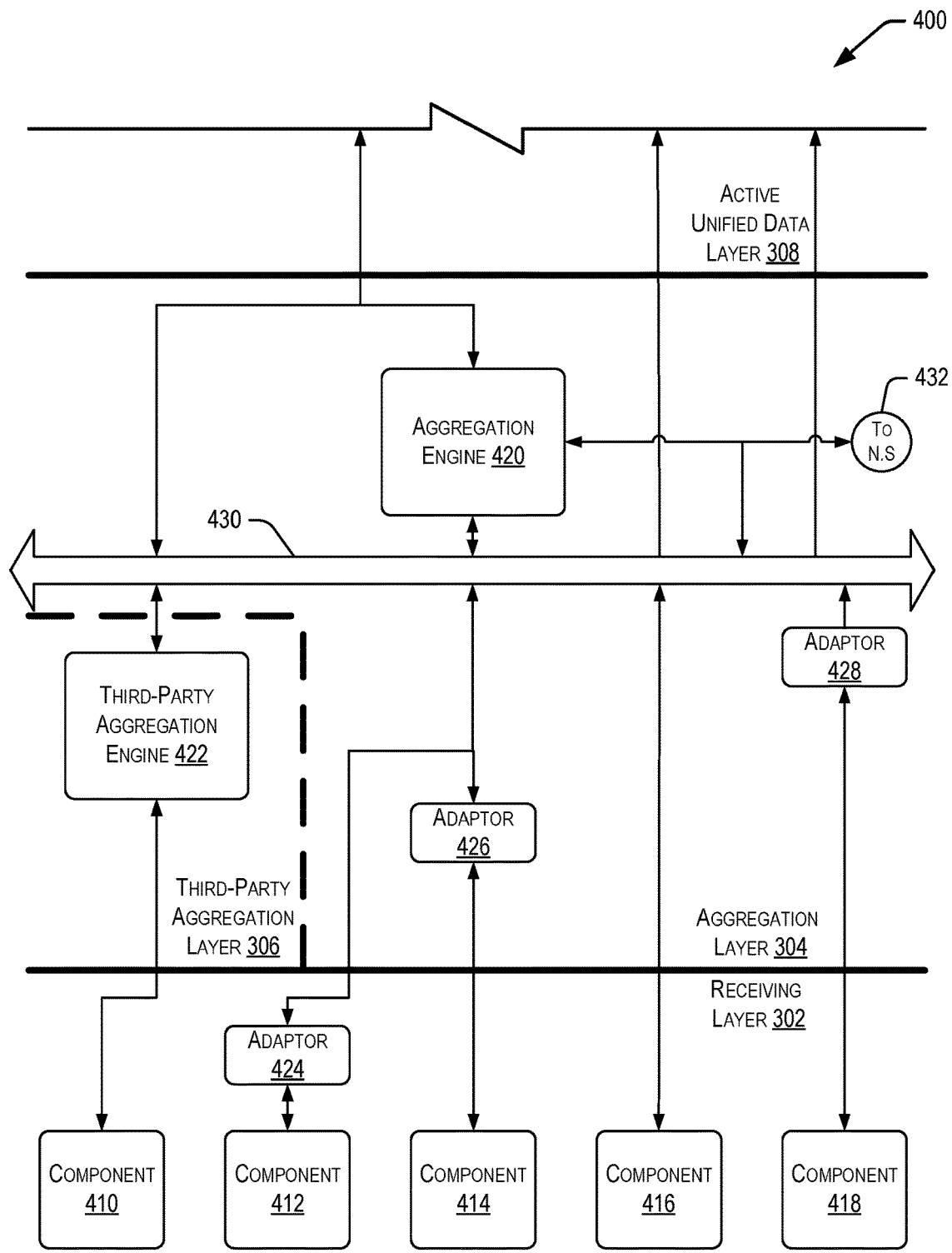
FIG. 4 is an example schematic model illustrating an aspect of the network communication model of FIG. 3 in more detail.

Turning next to FIG. 4, a diagram 400 is shown that depicts a portion of the medical architecture stack 300 according to an embodiment of the invention. In particular, the diagram 400 includes the receiving layer 302, the aggregation layer 304, the third-party aggregation layer 306, and a portion of the active unified data layer 308. The receiving layer 302 receives data from one or more components 410-418. The components 410-418 are examples of the one or more generation components 204. The components 410-418 may be spread across multiple medical care facilities within a single or multiple medical provider organizations. For example, the component 410 may be located at a hospital, the component 412 may be located at a clinic, the component 414 may be located at urgent care facility, and so forth. Additionally, the hospital may belong to a first medical provider organization, while the clinic may belong to a second medical provider organization, both of which or part of which may belong to the same medical provider network. In some examples, the components 410-418 may include complimentary layers to facilitate data transmission. For example, the components 410-418 may include a transmission layer, generation layer, and/or a receiving layer to communicate data at the receiving layer 302 and, in some examples, receive data from the receiving layer 302.

In some instances, two or more of the components 410-418 generate medical-related data according to different formats. The medical-related data can then be transformed, translated, or otherwise adjusted before an aggregation engine 420 (e.g., the aggregation engine 218) or a third-party aggregation engine 422 (e.g., the aggregation engine 218) collects the medical-related data. In some examples, the adjustment takes place within the receiving layer 302. Thus, an adaptor 424 is associated with the component 412 located in the receiving layer 302. The adaptor 424 is an example of the transformative adaptor 216. The adaptor 424 is implemented, as appropriate, in hardware, software, or any suitable combination of both. For example, the transformative adaptor 216 may be a bolt-on adaptor that adjusts medical-related data as such data leaves the component 412.

Other adaptors, such as adaptor 426 and adaptor 428, are implemented within the aggregation layer 304. These adaptors can function in a similar manner as the adaptor 424. In some examples, the medical-related data provided by the component 414 is transmitted through adaptor 426 prior to being directed to the aggregation engine 420. The medical-related data provided by the component 416 is transmitted through the aggregation layer 304 and/or enters the aggregation engine 420 without having first traveled through an adaptor. The medical-related data provided by the component 418 is transmitted through the aggregation layer 304 and through adaptor 428. In some examples, the component 418 provides for streaming of medical-related data. The medical-related data provided by the component 410 is transmitted directly to the third-party aggregation engine 422.

In some examples, medical related data provided by the components 410-418 may be communicated via a messaging bus 430 (e.g., the messaging bus 236). The medical-related date, in the form of medical messages may be put on the messaging bus 236 by the one or more components, by the aggregation engine 420, by the third-party aggregation engine 422, and by any other suitable device capable of generating medical messages. In some examples, medical messages are taken off of the messaging bus 430 by the aggregation engine and/or by one or more listeners described in more detail herein. Thus, circle 432 indicates that medical-related data (e.g., medical messages) may flow from the messaging bus 430 to a notification service and processed in accordance with techniques described herein.

The aggregation engine 420 and the third-party aggregation engine 422 function in a similar manner. In some examples, the third-party aggregation engine 422 is operated by a different entity than the entity that operates the aggregation engine 420 and may belong to different medical provider organizations or a different medical provider network. This may be because the medical-related data collected by the third-party aggregation engine 422 differs in some way from the medical-related data collected by the aggregation engine 420. In any event, the aggregation engine 420 is configured to perform integration of medical-related data, including generic integration. For example, the aggregation engine 420 performs one or more operations on medical-related data including tagging, logging, and protocol conversion. The aggregation engine 420 also supports one-to-many communications of medical-related data. In some examples, medical-related data flows between the aggregation engine 420, the third-party aggregation engine 422, and some of the components 410-418 and elements of the active unified data layer 308.

Figure 5:
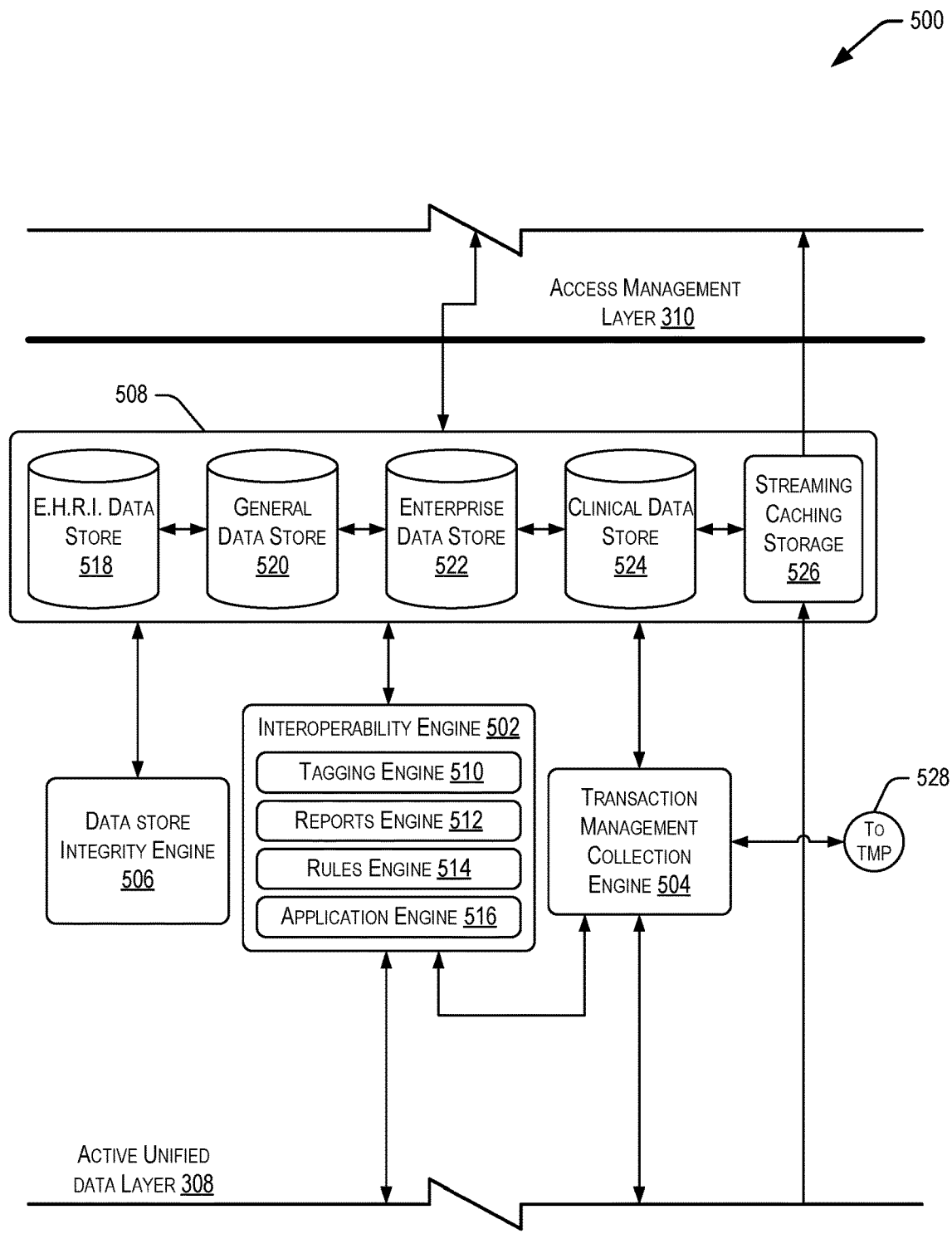
FIG. 5 is an example schematic model illustrating an aspect of the network communication model of FIG. 3 in more detail.

Referring next to FIG. 5, a diagram 500 is shown that depicts a portion of the medical architecture stack 300 according to an embodiment of the invention. In particular, the diagram 500 includes the active unified data layer 308 and a portion of the access management layer 310. The active unified data layer 308, as illustrated in the diagram 500, includes an interoperability engine 502 (e.g., the interoperability engine 220), a transaction management collection engine 504, a data store integrity engine 506, and a data store 508 (e.g., the data store 226). Generally, the interoperability engine 502 receives medical-related data from elements within the aggregation layer 304 (e.g., from the aggregation engine 420) and performs one or more operations with respect to the medical-related data. The interoperability engine 502 also facilitates storage of at least a portion of the processed information in the data store 508.

The transaction management collection engine 504 is implemented as part of the transaction management engine 104. The transaction management collection engine 504 is configured to generate message indicators identifying flows of data by and between elements of a medical provider network implemented using the techniques described herein. The flows of information include messages which include medical-related data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including medical-related data are transmitted from the aggregation layer 304. The table may be stored in association with the transaction management platform 528.

In some examples, the table also includes information for tracking the progress of the message from an origination node to a destination node. For example, typically when a message (e.g., any communication of data) is first received by the transformative integration engine 102 (e.g., the interoperability engine 502), the transaction management engine 104 (e.g., the transaction management collection engine 504 of the transaction management engine 104) may generate a unique identifier for the message in order to track that message as it moves throughout the medical provider network. The unique identifier may be included in the header of the message such that when the next node (e.g., component, device, server, etc.) after the transformative integration engine 102 receives the message, that node can report back to the transaction management engine 104 that it saw the message. In this manner, the transaction management engine 104 may enable end-to-end tracking of messages for the life of the message. In one example, the messages are pharmacy orders. The pharmacy orders may be generated by a user entering in the orders at one of the components. The orders may be received by the transformative integration engine 102 and integrated into the system. In some examples, the transaction management engine 104 may be notified that the orders have been received and may therefore be configured to generate message IDs for each order. These message IDs may then be associated with each of the orders. As the orders continue to move throughout the medical provider network (e.g., away from the transformative integration engine 102), the transaction management engine 104 may be track their movement using the message IDs. If one of the orders does not make it to its destination, the transaction management engine 104 (or part of the transaction management platform 528) may determine why the order was stopped. In some examples, this cause may be hardware related (e.g., an unplugged Ethernet cable, a broken router, etc.), software related (e.g., a router routing to the wrong location), or any other reason for orders not arriving at their correct destination.

In some examples, the transaction management engine 104 (e.g., the transaction management collection engine 504 of the transaction management engine 104) may receive the message and/or message identifier directly from one of the components 410-418. For example, one of the components 410-416 may be configured to generate the unique message identifier and/or communicate directly with the transaction management engine 104. The message also may travel via one or more intermediate odes on its way to the destination node. In some examples, a node is a component such as the components 410-418, which may be running an application. In some examples, the unique identifier and the routing of the message to its destination may stored in a table that also includes: a geolocation of each node, a network from which the message originated, a type of node, the unique node identifier, and a time associated with the message leaving the origination node. In some examples, the transaction management collection engine 504 provides unique message identifiers to other elements of the medical provider network to monitor the messages as they move throughout the medical provider network. The transaction management collection engine 504 also provides a portion of the unique message identifiers to a transaction management platform (indicated by circle 528) for further analysis of the message identifiers. Such analysis may include reconciliation of lost messages, latency reporting, audit management and compliance, and other such analyses.

As mentioned previously, the interoperability engine 502 is configured to store medical-related data in the data store 508. A plurality of sub-engines 510-516 of the interoperability engine 502 are configured to perform operations relating to storing medical-related data in the data store 508.

The interoperability engine 502 includes a tagging engine 510 configured to perform semantic tagging and indexing of medical-related data. The tagging engine 510 therefore is configured to receive medical-related data, read metadata associated with the medical-related data, semantically scan the content of the medical-related data, and associate one or more tags with the medical-related data. The tagging engine 510 may therefore have access to hundreds, thousands, or even more possible tags. These tags may have been input by users, learned, pre-defined, generated by outside third-party mapping sources, and/or gathered from other components and/or data stores of the medical provider network. For example, if the medical-related data is a medical chart for a cancer patient, the tagging engine may be configured to read any metadata associated with the chart to determine which tags may be appropriate to associate with the chart. From the metadata the tagging engine 510 may determine that the chart is for a cancer patient by reading metadata indicating that an author field is populated with the name of an oncologist who prepared the medical chart. The tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the medical care provider or medical care facility where the data originated, and other similar fields. The tags may be stored in association with the medical-related data (e.g., the chart) and/or may be stored independent from the medical-related data but include an identifier such that when searching tags the medical-related data may be capable of population.

Continuing with the example from above, if the medical-related data is a medical chart for a cancer patient, the tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by the tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of medical-related data. This meaning and/or context may assist the tagging engine 510 to determine one or more tags to associate with the medical-related data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, the tagging engine 510 may also index portions of the medical-related data within one or more data stores of the data store 508. In some examples, the such indexing may be based in part on the selected tags.

The interoperability engine 502 also includes an reports engine 512 configured to generate one or more reports or alerts based on medical-related data. For example, the reports engine 512 may generate reports when certain types of medical-related data are received or when medical-related data with certain characteristics is received. The reports engine 512 may also generate alerts. The reports and/or alerts generated by the reports engine 512 may be outputted in the form of one or more communications to an administrator, an authorized user, or other similar user via a user device. Such communications include, for example, signals, sirens, electronic notifications, popups, emails, text messages, and the like. Content of such communications may include information characterizing a care provider's or institution's performance in providing care, efficiency and/or patient outcomes; identifying concern patient-data patterns; identifying losses of medical-related data; and the like. In some examples, the content is presented in the form of one or more documents, tables, figures, charts, graphs, and the like. For example, the reports engine 512 may output a report to a hospital administrator indicating the patient outcomes for the hospital for the last year. This report may be presented in the form of a graph.

The interoperability engine 502 also includes a rules engine 514 configured to create and manage business rules, health-response rules, alert/reports rules, data-formatting rules, data-sharing rules, transmission rules, aggregation rules, user authorization rules, law-based rules, cost-based rules, and other similar rules. Such rules may be user-defined, fixed, learned by elements of the medical provider network, and any combination of the foregoing. For example, a business rule may be defined by a hospital administrator and relate to supply chain management and visualization and optimization of planning and scheduling. The rules can apply across different medical care facilities, medical conditions, patient types, geographic areas, and/or entities. Finally, the interoperability engine 502 includes an application engine 516 configured to provide service-oriented architecture web services.

The data store 508 includes an electronic health record information (EHRI) data store 518 ("the record data store 518"), a general data store 520, an enterprise data store 522, a clinical data store 524, and a streaming caching storage 526. While the data store 508 is illustrated as including a fixed number of data stores and storage elements, it is understood that the data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables (e.g., pertaining to a similar medical condition, treatment, physician or geographical region) but that differ in one or more other variables (e.g., institution affiliation). Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within the record data store 518 is retained medical-related data including electronic health record information. In some examples, the information within the record data store 518 is organized according to patient identifying information. Thus, the record data store 518, in some examples, includes individually identifiable information. But it may also include de-identified information.

Within the general data store 520 is retained medical-related data. The medical-related data may be stored in a relational database format or in any other suitable format. Thus, the data within the general data store 520 may be retained in a data structure that includes one or more tables capable of accessing each other. The general data store 520 includes certain types of clinical information. For example, the general data store 520 may include orderables and labs. In some examples, the general data store 520 includes medical-related data, including medical record information associated with patients, patient insurance information, demographic information of the patients, and at least some financial information of the patients. In some examples, the general data store 520 includes all medical-related data needed for clinical decision making as discussed herein. In some examples, the general data store 520 includes a subset of the information that is included in the enterprise data store 522.

Within the enterprise data store 522 is retained medical-related data in a relational database format. Thus, the data within the enterprise data store 522 may be retained in a data structure that includes one or more data structures (e.g., tables) capable of accessing each other. The enterprise data store 522 is an example of an enterprise data warehouse. In the enterprise data store 522 is joined many different types of medical-related data. For example, clinical, financial, and administrative information are stored in the enterprise data store 522. In some examples, the enterprise data ware house 522 includes medical-related data pertaining to clinical decision making as discussed herein and other medical-related data typically used by conventional business concerns. Thus, in the enterprise data ware house 522 may be combined clinical decision making information and business operations information. For example, the enterprise data warehouse 522 may include financial information, supply chain information, business units organization information, clinical organization information, human resources information, and any other suitable type of information relevant to the operations of a medical care organization as a business concern, whether non-profit or for profit.

Within the clinical data store 524 is retained medical-related data in a non-relational database format. Thus, the data within the clinical data store 524 may be retained in a structure other than tables. Such structure may be appropriate for large and complex data sets including medical-related data. In some examples, the clinical data store 524 (or any other data store) may be a unified system for clinical information, which may include: a document-centric, schema-agnostic, structure-aware, clustered, transactional, secure, database server with built-in search and a full suite of application services. An example of such a unified system may be Marklogic. The clinical data store 524 can support data aggregation, data organization, data indexing, data tagging and mapping to semantic standards, concept matching, concept extraction, machine learning algorithms, concept discovery, concept mining, and transformation of personal medical record information. In some examples, clinical data store 524 includes medical-related data pertaining to clinical decision making (similar to the general data store 520) as discussed that is organized and accessed in a different manner. For example, the medical-related data within the clinical data store 524 may be optimized for providing and receiving information over one or more health information exchanges. In some examples, such organization may mean that less demographic information is associated with each patient, or only a portion of financial information is associated with each patient. In some examples, the clinical data store 524 includes a subset of the information that is included in the enterprise data store 522.

Finally, in some examples, the streaming caching storage 526 is a streaming data cache data store. As discussed previously, certain components of the components 410-418 may support streaming data to other components or user devices. The streaming caching storage 526 is a location where streaming data can be cached. For example, assume that the component 418 is an MRI machine operated by a technician in hospital A and that a doctor using a computer in hospital B desires to view a live or substantially live stream of the MRI results. The component 418 can send a portion of data to the streaming caching storage 526 which can retain the portion of the data for a certain period of time (e.g., 1 day). Thus, the streaming caching storage 526 is configured to cache data that can be streamed.

The diagram 500 also includes data store integrity engine 506. In some examples, the data store integrity engine 506 is configured to ensure integrity of the information within the data store 508. For example, the data store integrity engine 506 applies one or more rules to decide whether information within all or part of the data store 508 should be scrubbed, removed, or adjusted. In this manner, confidence is increased that the information within the data store 508 is accurate and current.

Figure 6:
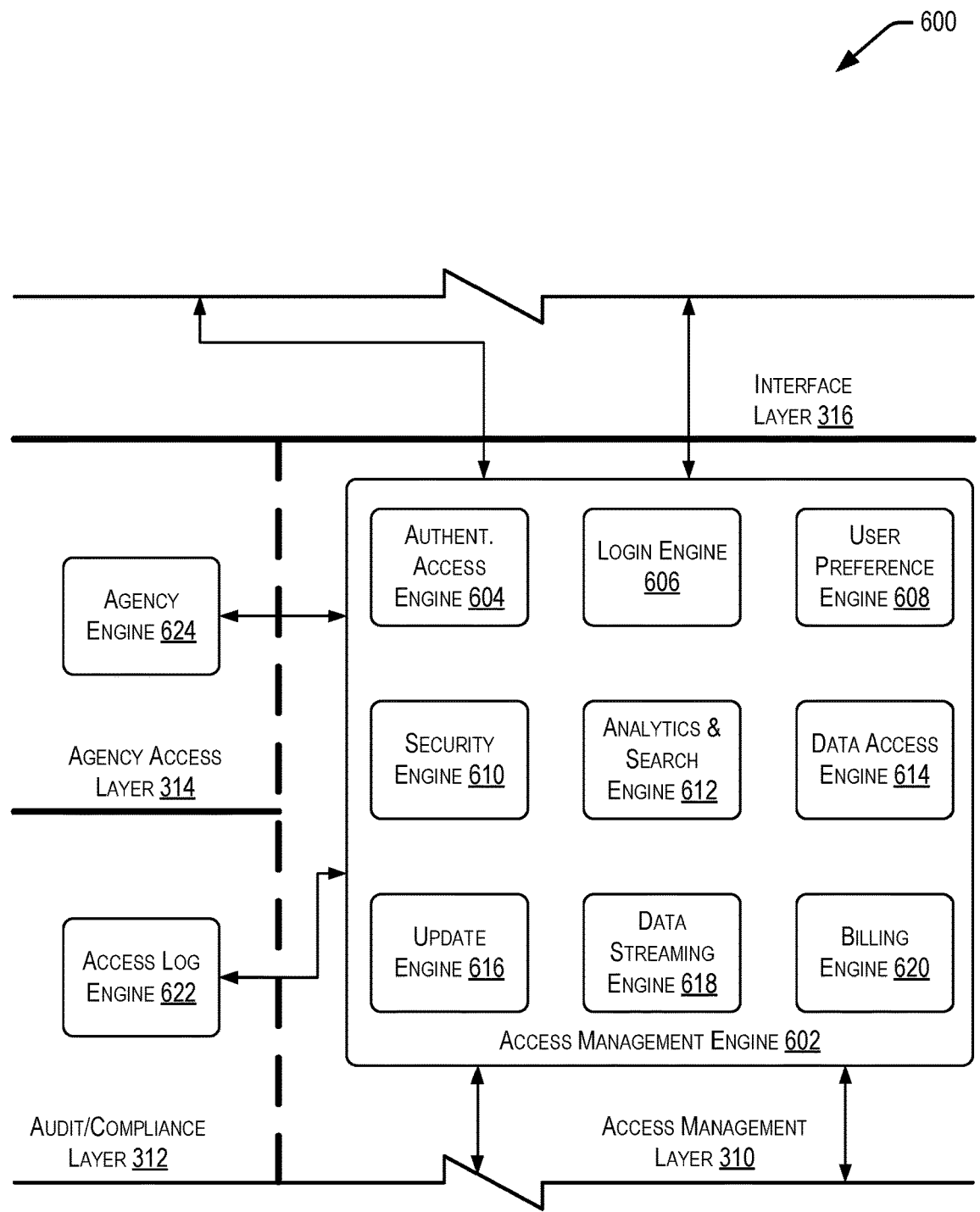
FIG. 6 is an example schematic model illustrating an aspect of the network communication model of FIG. 3 in more detail.

FIG. 6 shows a diagram 600 which depicts a portion of the medical architecture stack 300 according to an embodiment of the invention. In particular, the diagram 600 includes the access management layer 310, the audit/compliance layer 312, the agency layer 314, and a portion of the interface layer 316.

The access management layer 310, as illustrated in the diagram 600, includes an access management engine 602. The access management engine 602 is an example of the access management engine 222. Generally, the access management engine 602 can be configured to manage access to elements of the transformative integration engine 202 by different components, applications, and user devices.

The access management engine 602 within the access management layer 310 also provides functionality similar to an operating system. For example, the access management engine 602 includes a plurality of engines configured to manage different aspects of interacting with elements of the medical provider network. For example, a user who desires to access portions of medical-related data retained in the data store 508, may do so by interacting with the access management engine 602 using one or more applications (not shown). Thus, the access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, a streaming data engine 618, and a billing engine 620. The different engines of the access management engine 602 can define routines, protocols, standards, and the like for interacting with elements of the medical provider network.

Beginning first with the authentication access engine 604, the authentication access engine 604 evaluates the rules and conditions under which users may access elements of the medical provider network; in particular, the conditions under which users may access medical-related data within the data store 508. These rules and conditions may be user-defined (e.g., by an administrator or reviewer), learned over time, and/or may be dynamically updated and/or evaluated based on characteristics of the user or the user's device attempting to access the medical provider network. The rules and conditions may indicate the types of users who have particular types of access within the medical provider network. For example, hospital administrators may have a different type of access from a patient. The type of access may also relate to the degree to which data is identified/de-identified. For example, a doctor to whom a release has been given, may have access to all of a patient's medical record. Similarly, a researcher may have access to the records for many patients, so long as the records are do not include identifying information. In some examples, a user desiring access to medical-related data provides certain identifying information and the authentication access engine 604 authenticates an identity of the user. For example, suppose the user is a doctor and the access is to medical charts for one of the doctors patients. To authenticate the doctor's identity, he or she provides identifying information and once validated can be granted access to elements of the medical provider network where such information may be stored.

The login engine 606 evaluates the rules and conditions under which users are able to log in to the medical provider network or access applications associated with the medical provider network. These rules and conditions may be user-defined (e.g., by an administrator), learned over time, and also may be dynamically updated and/or evaluated based on characteristics of the user or the user's device attempting to access the medical provider network. Thus, while the authentication access engine 604 evaluates the rules to determine which users may access the medical provider network, the login engine 606 evaluates the particular credentials, profiles, etc. of the users. For example, the login engine 606 can confirm that an entered username (e.g., and password), provided biometric data or code or identifier in a scanned tag or badge matches that in an authorized user data structure.

The login engine 606 evaluates one or more user profiles associated with each authenticated user. In some examples, a user profile includes a username, password, and other information associated with the user. For example, a user profile may indicate characteristics about the user (e.g., that the user is patient belonging to a particular doctor, that the user is an employee belonging to a particular medical care facility, that the user is a vendor seeking access to certain portions of the medical provider network, that the user is a doctor having a particular specialty, that the user is a scheduler who belongs to a clinic, and other characteristics).

The user preference engine 608 evaluates the rules and conditions under which user are able to store and update one or more user preferences corresponding to access of the medical provider network or access to applications associated with the medical provider network. These rules and conditions may be user-defined (e.g., by the user or administrator), and may include rules for default preferences. For example, using the user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

The security engine 610 evaluates the rules and conditions for ensuring the security of access to the elements of the medical provider network. In some examples, these rules and conditions are determined by administrators of the medical provider network. In some examples, the security engine 610 provides a plurality of computer virus protection services. These services can be called up and implemented when accessing the medical provider network or accessing applications associated with the medical provider network. The rules and conditions may be based on roles, based on profiles, based on domains, and any other suitable security configuration. For example, because the medical provider network may include sensitive medical-related data, the security engine 610 may enforce a domain-based rule that protects certain sensitive information (e.g., identifying information).

The analytics and search engine 612 evaluates the rules and conditions under which users can search for data within the medical provider network and access analytics relating to the medical provider network. In some examples, these rules and conditions are user-defined or learned over time in accordance with search engine optimization techniques. For example, the analytics and search engine 612 is used to search within the data store 508 for particular medical-related data. The analytics and search engine 612 supports any conventional searching algorithms. For example, the search engine 612 can be used to search within various fields and potential field values (e.g., Hospital field, state field, specialty field, diagnosis field, health outcome field, doctor field). In some examples, search engine 612 can provide analytics, such as statistics, graphs, distributions and/or comparative analysis pertaining to particular entities and/or medical characteristics. Such information may be selected by a user and presented on a user interface.

The data access engine 614 evaluates the rules and conditions under which users may operation in order to access particular medical-related data within the data store 508. In some examples, these rules and conditions are user-defined or learned over time. For example, the data access engine 614 may indicate the routines, subroutines, or other logic needed for an application to access certain portions of the data store 508. For example, while the authentication access engine 604 and the login engine 606 may manage which users can access parts of the medical provider network, the data access engine 614 may manage how authenticated users access data within the data store 508. To this end, the data access engine 614 may enforce and/or evaluate certain rules managing how users access different components of the medical provider network. In some examples, the data access engine 614 may be used to actually access data within the data store 508 (e.g., extract, download, or otherwise access). In some examples, the data access engine 614 may define procedures, protocols, and the like for accessing data. The protocols and procedures for accessing the data access engine 614 (like the other engines of the access management engine 602) may be provided to developers in the form of a software development kit (SDK). SDKs may enable developers write applications that can effectively communicate with elements (e.g., the data store 508) of the medical provider network. In particular, applications that can access a portion of the medical-related data stored within the active unified data layer 308.

The update engine 616 evaluates the rules and conditions for providing updates to other engines within the access management engine 602, plug-ins for applications that access the medical provider network, and for other similar elements of the medical provider network. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

The streaming data engine 618 defines the rules and conditions for enabling streaming of medical-related data between components and user devices of the medical provider network. For example, the streaming data engine 618 may enable the component 414 to stream medical-related data. Streamed data may include live or substantially live audio or video feeds, results of medical tests, output from medical equipment or devices, and any other suitable type of medical-related data capable of being streamed. In some examples, the data may be streamed to other components or user devices within the medical network or outside the medical network. In order to establish a streaming transmission, the streaming data engine 618 may identify a streaming destination and a streaming origin. Next, the streaming data engine 618 may pair the two and enable streaming. This may include allocated bandwidth within one or more network devices associated with the medical provider network. The streaming data engine 618 may also adjust the quality of the streaming data based on the availability of bandwidth. In some examples, the streaming data engine 618 may receive incoming streams (and continuously present the stream or monitor for particular data (e.g., exceeding a threshold, exhibiting an above-threshold change, having a particular value)).

The billing engine 620 evaluates the rules and conditions under which applications and users that access the medical provider network are billed. For example, the billing engine 620 may include a variety of different charging rules to be applied to applications and users. An example rule indicates that applications or users will be charged on an hourly basis, another indicates that applications or users will be charged on a data transfer basis in terms of bytes, and another indicates that the applications or users will be charged a single amount for unlimited use. The billing engine 620 also indicates, not only how applications and users are charged, but also how they billed (e.g., periodically, directly to users, to an organization, etc.). The billing engine 620 may also indicate how medical bills are calculated, compiled, and determined for users of the medical provider services and include the procedures for accessing one's bill. For example, the billing engine 620 may enforce billing structures rules for certain services provided by medical care professionals at medical care facilities. The billing engine 620 may also define the rule under which users (e.g., patients, doctors, nurses, etc.) may access their own bills and bills associated with others. In some examples, this may include stripping away certain protected-health information, identifying information, and the like. The engines of the access management engine 602 are accessed via the interface layer 316 discussed later.

Within the audit/compliance layer 312 is located an access log engine 622. The access log engine 622 evaluates the rules and conditions for logging access to the medical provider network by users, applications, devices, and the like. Logging access includes, in some examples, logging data conventionally collected by access log engines running in similar environments. Access log engine 622 can use this data to generate and transmit reports, for example, to stakeholders of the medical provider network such that they can make informed decisions regarding that is accessing the medical provider network and for what purposes.

Within the agency layer 314 is located an agency engine 624. The agency engine 624 evaluates the rules and conditions under which agencies can access the medical provider network. For example, agencies that may use the agency engine 624 include agencies to which the medical provider network provides compliance, tracking, or other reporting information. For example, the agency engine 624 may be used to track one or more performance indicators identified by a government agency, to report occurrences of infectious diseases, and to provide other similar reporting. Thus, in some examples, a government agency uses the agency engine 624 to collect data pertaining to compliance of the medical provider network with one or more statutes or regulations. In some examples, a university is an agency that uses the agency engine 624 to collect data pertaining to one or more studies. In some examples, the agency engine 624 can identify one or more entities (e.g., governmental agencies) that are to receive reports pertaining to medical operations or events and what types of data are to be reported to those entities. The agency engine 624 can then collect the pertinent data, potentially format and/or analyze the data, and facilitate transmission of (e.g., raw, formatted and/or analysis of) the data to the appropriate agency.

Figure 7:
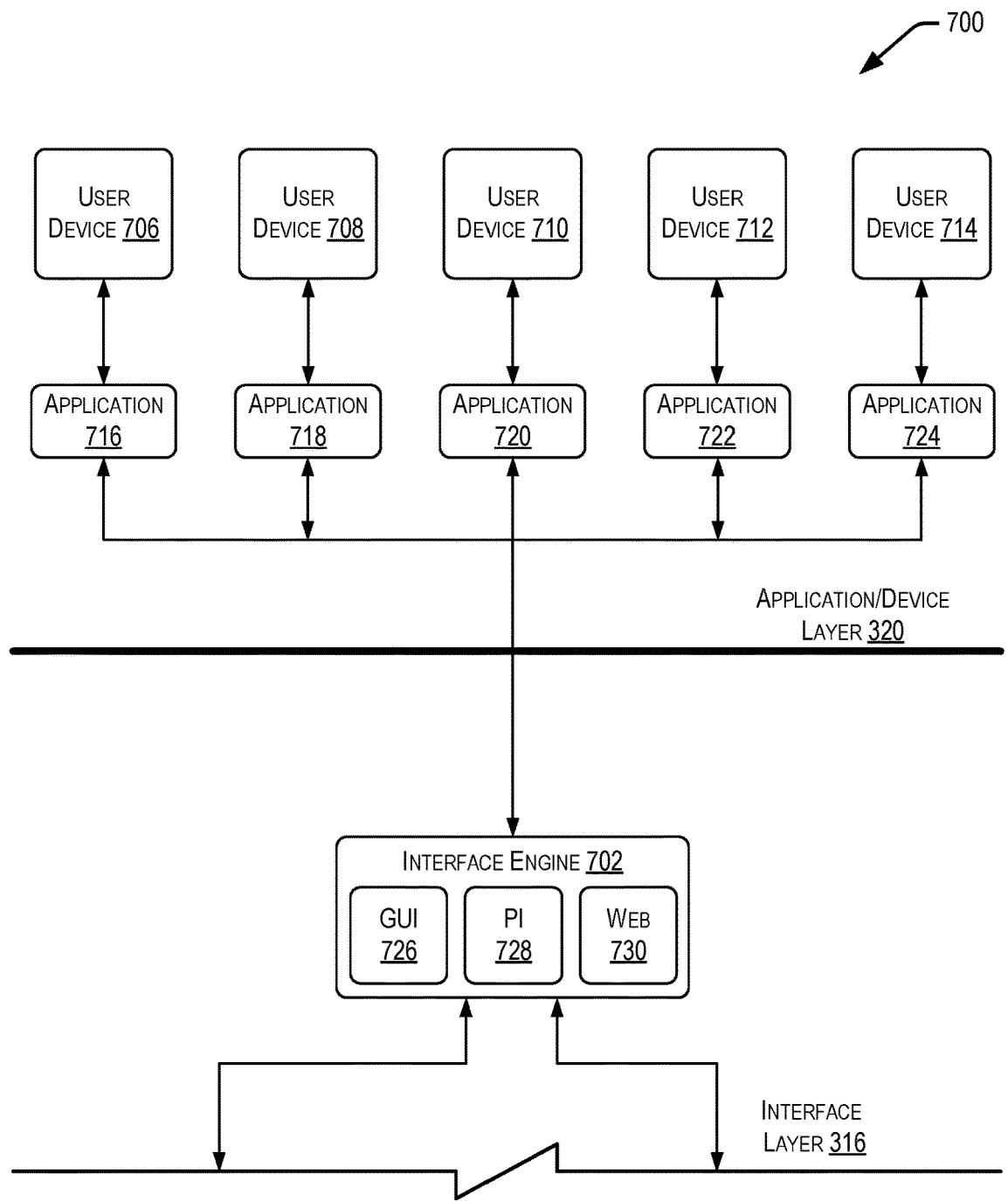
FIG. 7 is an example schematic model illustrating an aspect of the network communication model of FIG. 3 in more detail.

FIG. 7 shows a diagram 700 which depicts a portion of the medical architecture stack 300 according to an embodiment of the invention. In particular, the diagram 700 includes the interface layer 316, and the application/device layer 320. Within the interface layer 316 is located interface engine 702 (e.g., the interface engine 224). The interface engine 702 is configured to generate one or more interfaces (e.g., graphical user interface 726, programmatic interface 728, and/or web interface 730) to enable medical-related data to flow to user devices 710, 712, and 714 via respective applications 720, 722, and 724. In some examples, the interfaces of the interface engine 702 are embodied in hardware, software, or some combination of both. Within the interface layer 316 communications and inputs directed to interacting with elements of the access management layer 310 may be embodied.

The graphical user interface 726 is any suitable graphical user interface configured to interact with elements of the medical provider network. The programmatic interface 728 includes an application programming interface, a programmatic user interface, and other similar interfaces for defining core functions for accessing elements of the medical provider network. For example, the programmatic interface 728 may specify software components in terms of their operations. The web interface 730 is any suitable web interface configured to interact with elements of the medical provider network. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, medical devices capable of capturing inputs, and the like) operated by one or more users of the user devices 706-714. Output may be provided via one or more output devices (e.g., a display or speaker).

The interface engine 702 is utilized by applications internal to the medical provider network and external to the medical provider network to access medical-related data. In some examples, the applications that are internal include applications that are developed for internal use by employees, patients, nurses, medical care professionals, medical care providers, contractors, and others associated with the medical provider network. In some examples, the applications that are external to the medical provider network include applications that are developed for external use by those that are not associated with the medical provider network.

Generally, within the application/device layer 320, the applications 716-724 which communicate with other elements of the medical architecture stack 300 using the interfaces generated by the interface engine 702 are defined. This includes detailing how the applications 716-724 are to interact with the interfaces generated by the interface engine 702 for accessing medical-related data. For example, interacting may include accepting inputs at the user devices 706-714 to access medical-related data and, in response, providing the data, prompts, or other types of interaction with one or more users of the user devices 716-714. Thus the applications 716-724 may be related to one or more of the interfaces generated by the interface engine 702. For example, the application 720 may be interact with a graphical user interface (whether generated by the interface engine 702 or otherwise) to interact with other elements of the medical provider network. Interacting may include receiving inputs at the graphical user interface via the application 720, providing output data (e.g., medical-related data including reports, data sets, patient record information, diagnosis information, treatment care information, and the like) to the graphical user interface via the application 720, enabling interaction with other user devices, other applications, and other elements of the medical provider network, and the like. For example, some of the inputs may pertain to aggregation of medical-related data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of the applications 720, 722, and 724. In some examples, the applications 720, 722, and 724 include a variety of different applications that can be designed for particular users and/or uses. In one example, the application 720 is specific for doctors. In this example, the application 720 includes dashboards, widgets, windows, icons, and the like that are customized to the individual doctor. In some examples, the application 720 may present different medical-related data depending on a specialty associated with the doctor and protected health information associated with the doctor's patient. In this manner, the application 720 adapts and automatically adjusts depending on the context in which the doctor is using the application. In some examples, the medical-related data indicates performance statistics for the doctor, metrics relating to where the doctor falls along a distribution of other similar doctors, outlier patients, trends in diagnosis numbers and release, rapid changes in health-related values for the doctor's patients compared to other similar patients, and the like. The application 720 may be configured to receive input, adjust presentations, present unprompted alerts, adjust display of content, move more relevant content to the foreground, move less relevant content to the background, populate forms for the doctor to order tests, and the like.

In another example, the application 722 may be specific for nurses or types of nurses. In this example, the application 722 may include dashboards, widgets, windows, icons, and the like that are customized to individual nurses. Similar to the example discussed above pertaining to the doctor, in some examples, the application 724 may present different medical-related data depending on a position of the nurse. In this manner, the application 722 adapts and automatically adjusts depending on the context in which the nurse is using the application. For example, the nurse may receive medical-related data, such as test results for a patient. In some examples, the application 722 (or any other application) may be configured to operate on a mobile device.

In some examples, the application 724 may be a multi-role application for administrators and is used to manage patients and others that constitute the population of the entities or organizations within the medical provider network. Similar to the other examples discussed, in some examples, the application 724 may present different medical-related data depending on a role of the user who is using the application 724. In this manner, the application 724 adapts and automatically adjusts depending on characteristics of the user who is using the application 724. In this manner, the application 724 provide different medical-related data depending on the role of the user. For example, to an administrator may be presented identifying or de-identified information that characterizes overall flow of patients within a hospital (e.g., intake date, insurance, bed location, expected checkout date, etc.).

In some examples, the application 724 may be a business intelligence application. In this example, the application 724 is used to display business information generated by components of the medical provider network. This business information can be used for operations, planning, and forecasting. Such business information may include medical-related data because such data may impact operations, planning, forecasting, and the like. Accordingly, the application 724 may present de-identified information in the form of one or more metrics, indicators, or the like as they pertain to business intelligence.

The applications 716 and 718 shown in connection with the interface engine 702 are applications developed by third-parties. In some examples, such applications include any suitable application that benefits from accessing medical-related data. For example, the application 716 may be a health application, a nutrition application, a fitness application, and other similar applications. The medical provider network may include medical-related data pertaining to hundreds of thousands of patients. Having data pertaining to so many patients presents security concerns. For example, much of the medical-related data may be identifying data. Certain disclosure laws may prohibit the disclosure of such information. Accordingly, data that may be accessed by the applications 716 and 718 may be limited. In some examples, a patient of the medical provider network may use one of the applications 716, 718 to access his or her own medical-related data. In this example, the identity of the patient may be verified in accordance with techniques described herein.

The user devices 706-714 are any suitable user devices capable of running the applications 716-724. The user devices 706-714 are examples of the user device 228. In some examples, the user devices include: mobile phones, tablet computers, laptop computers, wearable mobile devices, desktop computers, pagers, and other similar user devices. In some examples, at least some of the user devices 706-714 are the same devices as at least some of the one or more components 410-418. In some examples, the user devices 706-714 may include complementary layers to the application/device layer 320 and/or the receiving layer 302. For example, the user devices 706-714 may include a transmission layer, a generation layer, and/or a receiving layer to communicate data at the application/device layer 320 and at the receiving layer 302.

Figure 8:
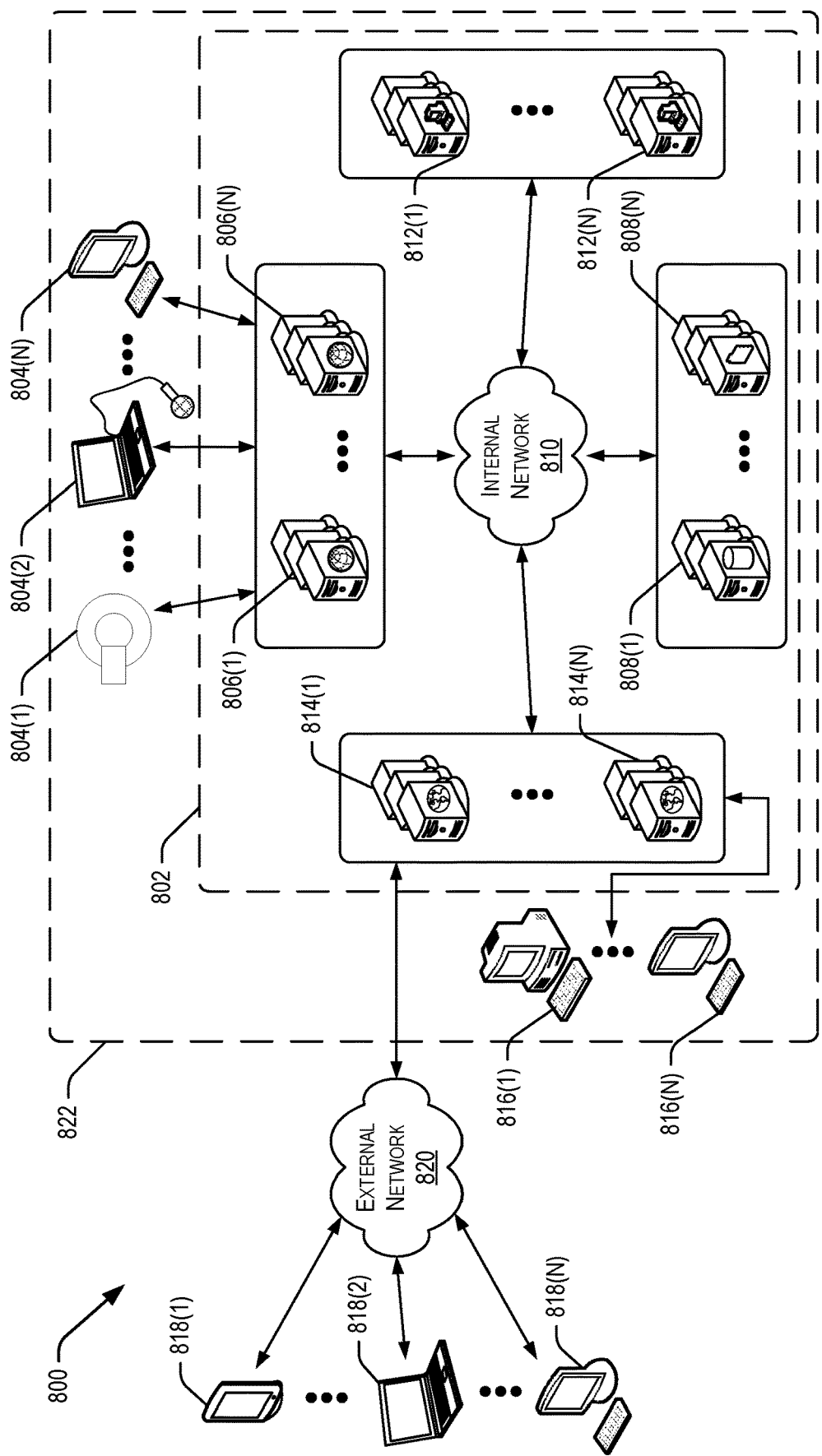
FIG. 8 is an example schematic architecture illustrating a network in which techniques relating to initiating message listening and routing message content to authorized user devices as described herein may be implemented, according to at least one example.

Turning now to FIG. 8, a medical provider network 800 is shown in accordance with an embodiment of the invention. The medical provider network 800 includes an internal organization 822 including a transformative integration engine 802. The transformative integration engine 802 is an example of the transformative integration engine 202 previously discussed. The medical provider network 800 is illustrated as an example configuration for implementing the techniques described herein. In particular, a configuration of elements as illustrated in FIG. 8, at least in some examples, communicates according to the layers of the medical architecture stack 300. For example, the internal organization 822 includes generation components 804(1), 804(2), and 804(N) which provide medical-related data to aggregation servers 806(1)-806(N).

The generation components 804(1), 804(2), and 804(N) operate in accordance with the receiving layer 302. In some examples, the generation component 804(1) is an Mill machine, a type of medical equipment, the generation component 804(2) is computer with a data collection device, a type of lab system, and the generation component 804(N) is a terminal, which is a type of business component or clinical component. The aggregation servers 806(1)-806(N) operate in accordance with the aggregation layer 304. The aggregation servers 806(1)-806(N) share medical-related data with data storage servers 808(1)-808(N) via one or more internal network(s) 810. In some examples, the internal network 810 is any suitable network capable of handling transmission of medical-related data. For example, the internal network 810 may be any suitable combination of wired or wireless networks. In some examples, the internal network 810 may include one or more secure networks. The data storage servers 808(1)-808(N) are configured to store medical-related data in accordance with the active unified data layer 308. The data storage servers 808(1)-808(N) include database servers, file storage servers, and other similar data storage servers.

Access management servers 812(1)-812(N) manage access to the medical-related data retained in the data storage servers 808(1)-808(N). The access management servers 812(1)-812(N) communicate with the other elements of the medical provider network 800 via the internal network 810 and in accordance with the access management layer 310.

Interface servers 814(1)-814(N) provide one or more interfaces applications to interact with the other elements of the medical provider network 800. The interface servers 814(1)-814(N) provide the one or more interfaces and communicate with the other elements of the medical provider network 800 via the internal network 810 and in accordance with the interface layer 316. The interfaces generated by the interface servers 814(1)-814(N) can be used by internal user devices 816(1)-816(N) and external user devices 818(1), 818(2), and 818(N) to interact with elements of the medical provider network 800.

The internal user devices 816(1)-816(N) are examples of the user devices 706-714. In some examples, the internal user devices 816(1)-816(N) run applications for patients, doctors, specialists, nurses, administrative professionals, network administrators, business leaders, and others that access the other elements of the medical provider network 800 via the interfaces generated by the interface servers 814(1)-814(N). As an additional example, the external user devices 818(1), 818(2), and 818(N) run applications developed by third parties for patients, doctors, specialists, nurses, administrative professionals, network administrators, business leaders, and others that access the other elements of the medical provider network 800 via the interfaces generated by the interface servers 814(1)-814(N).

The external user devices 818(1), 818(2), and 818(N) access the interfaces via external network 820. In some examples, the external network 820 is an unsecured network such as the Internet. The external user devices 818(1), 818(2), and 818(N) are examples of the user devices 706-714. The external user device 818(1) is a mobile device. In some examples, the mobile device may be configured to run an application to access the medical provider network 800. Similarly, the other external user devices 818(2)-818(N) run applications that enable them to access the medical provider network 800. While the medical provider network 800 is shown as implemented using discrete servers, it is understood that it may be implemented using virtual computing resources and/or in a web-based environment.

Embodiments herein are directed to a notification service. In particular, to a notification service that enables a user that is associated with a patient to sign up to receive notifications regarding treatment of the patient. For example, the notifications may indicate that an admitted patient has moved from a first room in a hospital to a second room in the hospital. To protect the privacy of the patient, a user that desires to receive notifications is subjected to an authorization process. During the authorization process, the identity of the user and/or an identify of the patient may be verified. For example, the requesting user may be required to provide personal information about the patient to the notification service. The notification service may then verify this personal information against comparable information on file for the patient. Once verified, the user can receive updates regarding the treatment of the patient. To determine when updates should be sent, the notification service monitors for certain events that would trigger notification. These events may be identified as one or more components of a messaging system monitor medical messages that flow over a messaging hub. Once a message is identified that is related to the patient, the notification service may determine whether report out a portion of the message, based at least in part on the substance of the message. In some examples, the notification service maintains a set of notification rules that define the circumstances under which a message may be provided in the form of a notification. To this end, the notification rules may be pre-defined, user-defined, learned, generated, or otherwise populated. In some examples, the notification rules may be specific to a particular patient (e.g., a first patient may authorize more information to be shared compared to a second patient) or to a particular group of patients (e.g., patients that are children may have particular rules specific for all children), and may also be generic for all users. For example, certain types of personal health information may never be reported out as a notification. In some examples, the notifications are sent via text message to a user device of the user.

Figure 9:
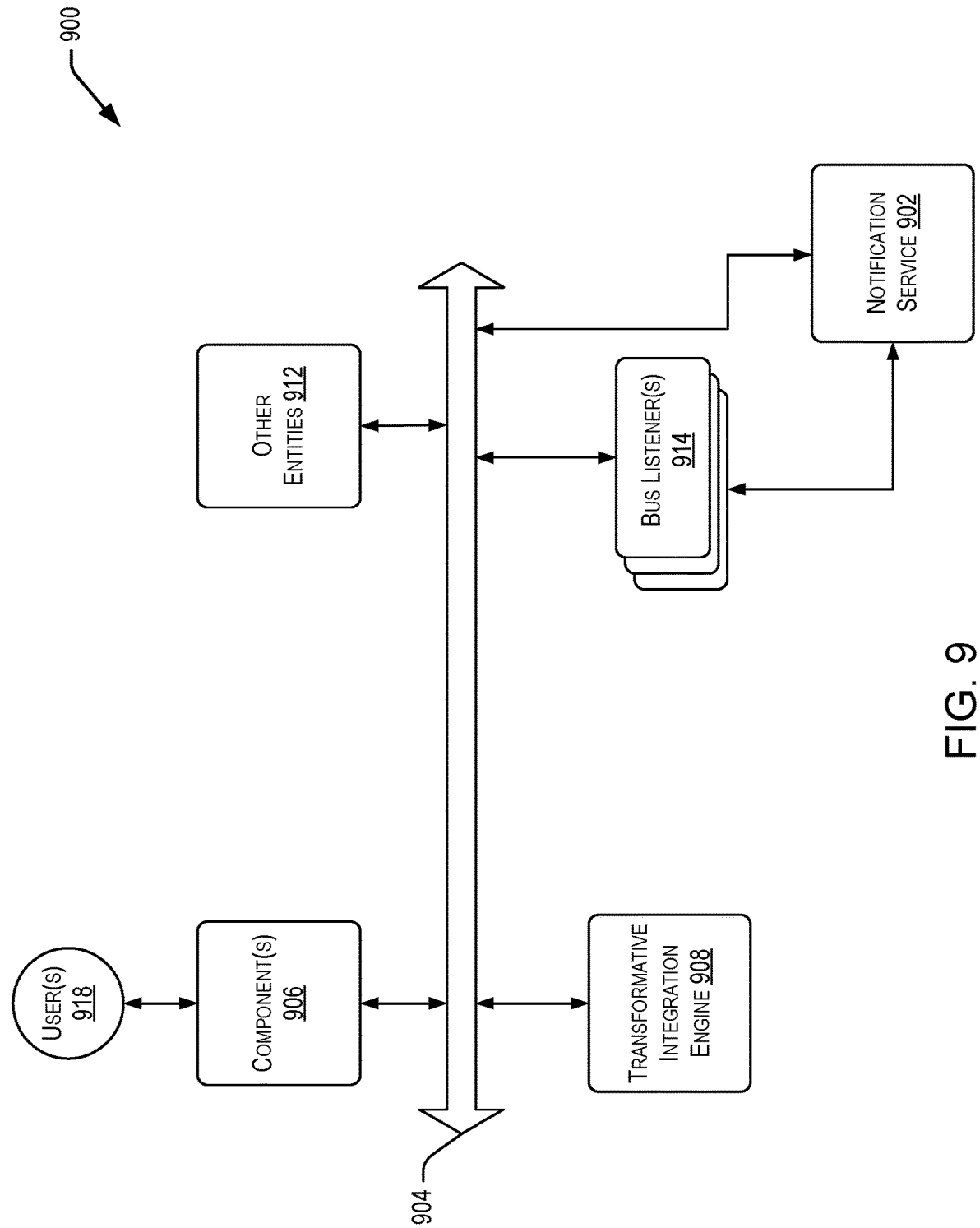
FIG. 9 is an example block diagram illustrating an environment in which techniques relating to initiating message listening and routing message content to authorized user devices as described herein may be implemented, according to at least one example.

Turning now to FIG. 9, a block diagram of a messaging system 900 of a medical provider network is shown in accordance with an embodiment of the invention. The messaging system 900 may be implemented using at least some of the elements of the medical provider network 800. The messaging system 900 includes a notification service 902 (e.g., the notification service 238), which is configured to implement the techniques described herein. The messaging system 900 includes the notification service 902 in network communication with a messaging bus 904 (e.g., the messaging bus 430). The notification service 902 is configured to implement the techniques described herein. For example, the notification service 902 may enable generation of notifications relating to the treatment of patients within a medical provider network.

The messaging bus 904 is any suitable combination of hardware and/or software configured to implement communication between different elements and applications of a network. For example, the messaging system 900 includes a number of elements in network communication with the messaging bus 904. In some examples, elements also include applications and/or the devices on which the applications are running. The elements include, for example, components 906 (e.g., the components 412), a transformative integration engine 908 (e.g., the transformative integration engine 102), other entities 912, and the notification service 902 in communication with the messaging bus 904 via bus listeners 914 and/or directly. Users 918 may utilize the components 906 and/or one or more applications running on the components 906 to generate medical messages. The users 918 are examples the medical professionals and other users who access the components 906 to generate medical messages as described herein. In some examples, certain ones of the components 906 generate medical messages without any one of the users 918.

In this manner, the messaging bus 904 allows the elements of the messaging system 900 to be easily plugged in and out (switched on and off) of the medical provider network (e.g., the medical provider network 800) without impact on other elements and without the need to restart the messaging system 900 or even stop running applications on the elements (e.g., the components 906). In some examples, the messaging bus 904 may function as a single message turntable between the elements of the messaging system 900. In effect, such functioning reduces the number of point-to-point connections between communicating elements of the messaging system 900. Thus, each element of the messaging system 900 directs its messages through the messaging bus 904 instead of going directly to the end point (e.g., a server, storage device, or other element). This indirection allows the messaging bus 904 to monitor and log the traffic. In this manner, the messaging bus 904 can intervene in message exchange.

The messaging bus 904 supports publish/subscribe functionality. In this manner, other elements of the messaging system 900 and other elements (not shown) may be provided with indications when certain messages having certain characteristics are passed over the messaging bus. For example, the bus listeners 914 are examples of elements that take advantage of the publish/subscribe functionality. The bus listeners 914 are examples of subscribers. The components 906, the transformative integration engine 908, and the other entities 912 are examples of publishers. However, in some examples, the components 906, the transformative integration engine 908, and/or the other entities 912 may have subscriber characteristics as well. For example, the other entities 912 may have their own bus listeners configured to listen for certain messages and provide the other entities 912 with the messages once identified. In any event, the bus listeners 914 may be configured to listen for specific messages. Once a particular message, for which one of the bus listeners 914 has been initiated, is put on the messaging bus 904 (e.g., "published"), the bus listener 914 can identify and retrieve the message from the messaging bus 904. Thus, the bus listener 914 can retrieve the message, even if the expected recipient of the message is unknown to the bus listener 914.

In some examples, a single bus listener 914 is initiated that for each patient whose records will be monitored by the notification service 902. For example, once a patient authorizes the notification service 902 to monitor his or her records, a bus listener 914 may be initiated and/or generated which listens for messages which include characteristics of the patient. Example characteristics include identifying and de-identified forms of personal health information (PHI). Once the bus listener 914 identifies a message which includes such characteristics, it makes it available to the notification service 916 for further processing. In some examples, the components 906 provide information to the messaging bus 904 directly or via some other device.

In some examples, the notification service 916 initiates a bus listener 914 to listen to the messaging bus 904 (i.e., to scan information going on to and off of the messaging bus 904) for a particular type of information (e.g., discharge information), information for a particular user (e.g., a patient), or the like. Once the bus listener 914 identifies the requested information, if authorized, the bus listener 914 can remove the information and provide it to the notification service 916. The notification service 916 can then processes the information. In some examples, once the bus listener 914 identifies the requested information, the bus listener 914 requests the providing element to provide the information to the notification service 916 (e.g., in a point-to-point fashion).

In some examples, the bus listeners 914 include one or more information barriers to ensure that PHI is not inappropriately shared with the other entities 912 or other elements of the messaging system 900. The one or more information barriers can include logical separations and/or physical separations. And while the messaging system 900 can includes enterprise level network security which is often reliable, certain elements of the messaging system 900 may not be subject to as much security scrutiny. As such, in some examples, the bus listener 914 is enabled to only read de-identified information.

In some examples, the other entities 912 and the users 918 (via the components 906) are in network communication with the messaging bus 904. The other entities 912 and/or the users 918 may be associated with a medical care organization which provides care to the patient. In some examples, each of the users 918 and/or the other entities 912 may provide and/or receive medical-related information in the form of medical messages. For instance, in some examples, each connection to the messaging bus 904 is an individual domain such that the other entities 912 and the components 906 communicate with the messaging bus 904 via different formats, proprietary protocols, varying encryption techniques, various languages, different machine languages, and the like. In some examples, the connections are dedicated and/or shared VPN tunnels. In some examples, the bus listeners 914 are configured to identify medical messages from the different other entities 912 and the components 906.

The other entities 912 may be, for example, an urgent care facility, an outpatient facility, a hospital, a clinic, a record service, or any other suitable entity which provides or receives medical-related data. In particular, the record service may include one or more servers configured to retain medical record for patients. In some examples, the medical records are updated at one of the other entities (e.g., a hospital) and provided to the record service via the messaging bus 904. In this manner, the bus listeners 914 can identify the movement of medical-related data in the form of medical messages relating to medical records of patients. In some examples, medical-related data from the other entities 912 (e.g., the record service) may flow toward the transformative integration engine 908 as described herein. In some examples, the components 906 and/or the users 918 may be located at one or more of the other entities 912. In this manner, the components 906 may generate medical-related data at the other entities 912.

In some examples, the notification service 902 is configured to maintain analytics relating to the process flow of patients through the individual systems of the other entities 912. For example, a hospital (an example of one of the other entities 912) is configured to track the progress of patient X as patient X moves through different stages of receiving medical services at the hospital. The hospital also provides this tracking information to the messaging bus 904, which is picked up by a previously-initiated bus listener 914 and, in turn, accessed by the notification service 916. The notification service 916 may then generate notifications, alarms, statuses, updates, reminders and the like to medical care professionals of the hospital or authenticated users relating to patient X's care.

An example flow of patient X's treatment begins as he or she is registered at the hospital. In connection with his or her admittance, the hospital enters into its system the record information relating to his or her admittance (e.g., referral, intake paperwork, nurse reports, doctor reports, etc.) and a patient flow for patient X is created. In this example, the patient flow identifies the anticipated milestones, events, and other indicia related to treatment of patient X at the hospital. The patient flow information is shared with the notification service 902 via the messaging bus 904. In some examples, the notification service 902 is requested to create patient flows for new patients of the hospital. With the patient flow information, the notification service 902 can initiate the bus listeners 914 to monitor and track the progress of patient X as he or she progress through his or her treatment at the hospital. In one example, after an x-ray is ordered for patient X, the notification service 902 learns of this order, and generally informs the hospital and/or directly informs medical care professionals associated with the hospital that the x-ray has been ordered and an estimated time for completion. If the x-ray is taking too long (e.g., patient X has been waiting longer than a pre-determined threshold), the notification service 902 notifies the hospital. In this manner, the notification service 902 monitors and manages process flows for patients of the hospital. In other embodiments, the notification service 902 monitors the flows for other patients of the other entities 912 of the messaging system 900.

In addition to monitoring the flow of patients and notifying the other entities 912 and/or the users 918, the notification service 902 provides notifications to the users 918 via the components 906 relating to the progress, status, and the like of patients associated with the medical record information. For example, the users 918 may be first responders and the components 906 may be radios. Once a first responders is verified by the notification service 902, the first responder may be enabled to receive medical-related data regarding a victim who the first responder is treating in the field.

Figure 10:
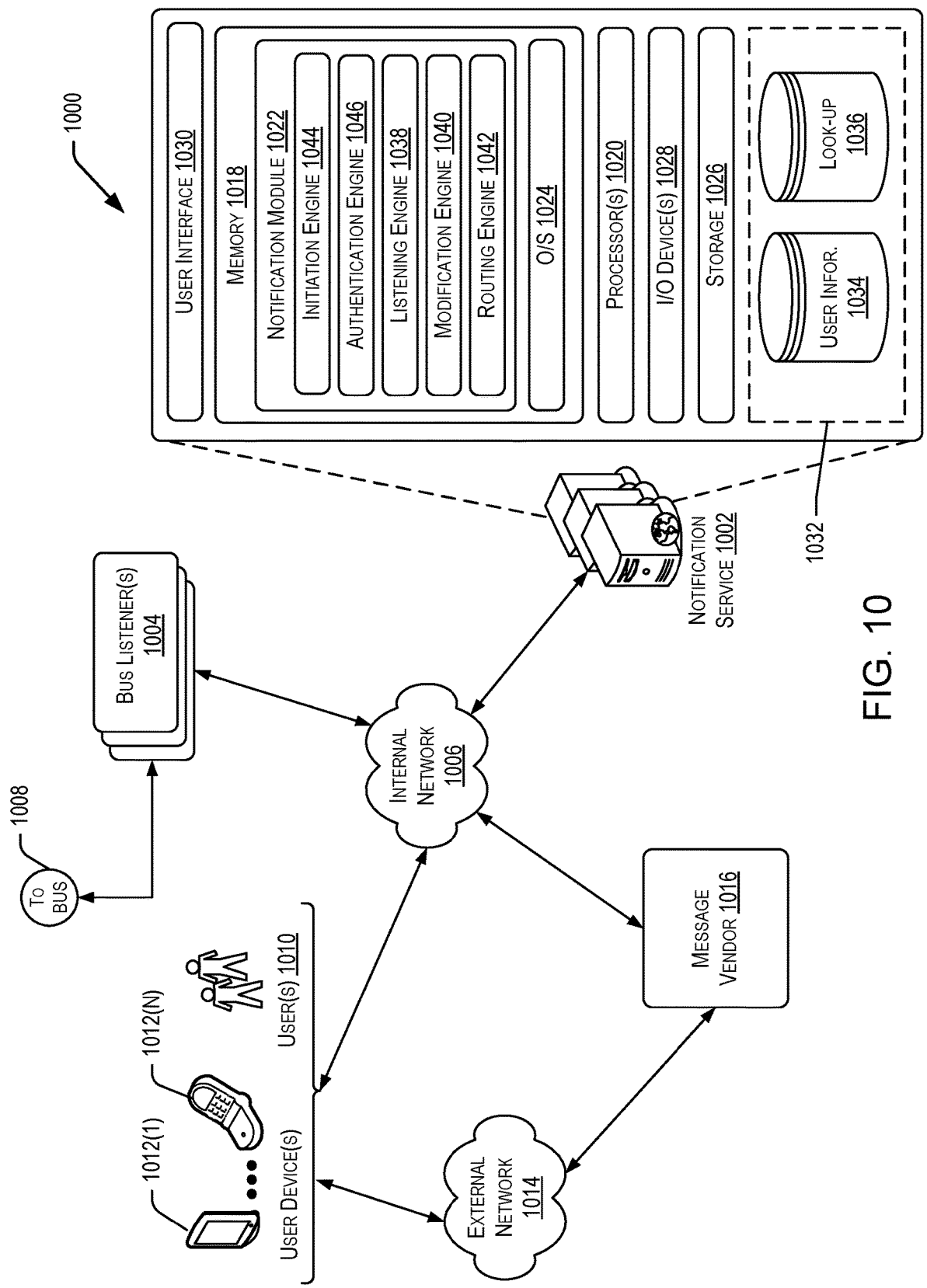
FIG. 10 is an example schematic architecture illustrating a network in which techniques relating to initiating message listening and routing message content to authorized user devices as described herein may be implemented, according to at least one example.

Turning next to FIG. 10, a block diagram illustrating a messaging system 1000 according to at least one example. The messaging system 1000 is an example of the messaging system 900 which illustrates other aspects in greater details. For example, the messaging system 1000 includes a notification service 1002 (e.g., the notification service 916) connected to bus listeners 1004 (e.g., the bus listeners 914) via an internal network 1006. The internal network 1006 is an example of a network that has restricted access. For example, when the techniques described herein are implemented at a single hospital, the internal network 1006 may be local area network within the hospital. When the techniques described herein are implemented in a medical care organization that includes many facilities, the internal network 1006 may be a network with enterprise level security appropriate for passing medical-related information.

As described herein, the bus listeners 1004 are in network communication with the messaging bus 904 (as indicated by circle 1008). In some examples, the messaging bus 904 is also in network communication with the internal network 1006.

The messaging system 1000 also includes users 1010 and user device 1012(1)-1012(N) (the user device(s) 1012). In some examples, the user devices 1012 are in network communication with the notification service 1002 via the internal network 1006. The user device 1012 may be any suitable device capable of communicating with the notification service 1002 and/or the message vendor 1016. For example, the user device 1012 may be any suitable computing device such as, but not limited to, a mobile phone, a smart phone, a personal digital assistant (PDA), a laptop computer, a personal computer, a desktop computer, a set-top box, a thin-client device, or other computing device. In some examples, the user device 1012 may be a cellular telephone. The user device 1012 may include a memory, a processor, a web-service application, a messaging application, and any other suitable feature to enable communication and interaction with the elements of the messaging system 1000.

For example, when the user 1010 is a medical care professional, perhaps as an employee of the medical care organization that hosts the notification service 1002, the medical care professional may be authorized to receive notifications regarding the treatment a patient of the medical care professional's via the internal network 1006. Because the internal network 1006 includes added layers of security compared to external network 1014, the notifications provided via the internal network 1006 may, in some examples, be more detailed compared to notifications provided via the external network 1014. For example, notifications provided via the internal network 1006 may include personal health information, while notifications provided via the external network 1014 may be stripped of any personal health information. In this manner, notifications may be provided to different ones of the users 1010 via different ones of the networks 1006, 1014.

The external network 1014 and/or the internal network 1006 may be any suitable network including, for example, any suitable combination of cable, cellular, radio, digital subscriber line, or any other suitable network, which may be wired and/or wireless.

In some examples, the messaging system 1000 also includes a message vendor 1016. In some examples, the message vendor 1016 is configured to provide notifications to the users 1010 via the user devices 1012. For example, the message vendor 1016 may a third-party which receives requests from the notification service 1002 and generates notifications that can be received by the users devices 1012. For example, the message vendor 1016 may provide notifications to the user device 1012 by accessing an address of the user device 1012 and generating a notification using one or more message services. The notification may be sent by the message vendor 1016 using a short message service (SMS), a multimedia message service (MMS), an instant messaging service, or any other suitable messaging service. In some examples, the message vendor 1016 receives the address of the user device 1012 from the notification service 1002 along with the notification. In some examples, the message vendor 1016 performs one or more operations on the notification prior to sending it out. For example, the message vendor 1016 may shorten the notification to comply with character restrictions. In some examples, the message vendor 1016 may send more than one notification based on a single notification received from the notification service 1002. In some examples, the message vendor 1016 has a virtual private network tunnel with the internal network 1006. In some examples, the message vendor 1016 is configured to encrypt messages prior to sending them to the user devices 1012. In this manner, the messages may carry more sensitive notifications (e.g., forms of personal health information) to the user devices 1012. In this example, the user devices 1012 may be appropriately configured to decrypt the messages received from the message vendor 1016.

In some examples, the message vendor 1016 is not included in the messaging system 1000. In this example, the notification service 1002 transmits messages directly to the user devices 1012 via the internal network 1006, the external network 1014, and/or any combination of the foregoing.

Generally, the notification service 1002 may be configured for implementing techniques relating to providing notifications as described herein. The notification service 1002 may include one or more computers, perhaps arranged in a cluster of servers or as a server farm, and may perform the computing techniques described herein. The notification service 1002 may therefore include at least one memory 1018 and one or more processing units (or processor(s)) 1020. The processor(s) 1020 may be implemented as appropriate in hardware, computer-executable instructions, software, firmware, or combinations thereof. Computer-executable instruction, software or firmware implementations of the processor(s) 1020 may include computer-executable or machine-executable instructions written in any suitable programming language to perform the various functions described. The memory 1018 may include more than one memory and may be distributed throughout the notification service 1002. The memory 1018 may store program instructions (e.g., the notification module 1022) that are loadable and executable on the processor(s) 1020, as well as data generated during the execution of these programs. Depending on the configuration and type of memory including the notification service 1002, the memory 1018 may be volatile (such as random access memory (RAM)) and/or non-volatile (such as read-only memory (ROM), flash memory, or other memory). The notification service 1002 may also include additional removable storage and/or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some examples, the memory 1018 may include multiple different types of memory, such as static random access memory (SRAM), dynamic random access memory (DRAM), or ROM. Turning now to the contents of the memory 1018 in more detail, the memory 1018 may include an operating system 1024 and one or more application programs, modules, or services for implementing the features disclosed herein including at least the notification module 1022 and its associated components.

In some examples, the notification service 1002 may also include additional storage 1026, which may include removable storage and/or non-removable storage. The additional storage 1026 may include, but is not limited to, magnetic storage, optical disks, and/or tape storage. The disk drives and their associated computer-readable media may provide non-volatile storage of computer-readable instructions, data structures, program modules, and other data for the computing devices. The memory 1018 and the additional storage 1026, both removable and non-removable, are examples of computer-readable storage media. For example, computer-readable storage media may include volatile or non-volatile, removable, or non-removable media implemented in any suitable method or technology for storage of information such as computer-readable instructions, data structures, program modules, or other data. As used herein, modules may refer to programming modules executed by computing systems (e.g., processors) that are part of the notification module 1022. The notification service 1002 may also include input/output (I/O) device(s) and/or ports 1028, such as for enabling connection with a keyboard, a mouse, a pen, a voice input device, a touch input device, a display, speakers, a printer, or other I/O device.

In some examples, the notification service 1002 may also include a user interface 1030. The user interface 1030 may be utilized by an operator, or other authorized user to access portions of the notification service 1002. In some examples, the user interface 1030 may include a graphical user interface, web-based applications, programmatic interfaces such as application programming interfaces (APIs), or other user interface configurations. The notification service 1002 may also include data store 1032. In some examples, the data store 1032 may include one or more databases, data structures, or the like for storing and/or retaining information associated with the notification service 1002. The data store 1032 may include data structures, such as user information database 1034 and look-up database 1036. While the data store 1032 is shown including only two databases (i.e., the user information database 1034 and the look-up database 1036), as would be recognized by one of ordinary skill in the art, the data store 1032 may include any suitable number of databases, including fewer than two or more than two.

The user information database 1034 may be used to store information about the users 1010 such as, for example, demographic information, medical information, record information, user preferences (e.g., language), contact information (e.g., a phone number), messaging information (e.g., length and frequency of notifications desired, types of notifications desired, etc.), and the like. Such users, include, for example patients, family members, medical care professionals, first responders, and the like. For example, within the user information database 1034 may be retained information describing those users which have signed up to receive notifications (e.g., authorized users) and user who have authorized notifications to be sent on their behalf (e.g., patients). In some examples, the look-up database 1036 includes information capable of identifying users based on de-identified information. For example, the look-up database 1036 can include a first column with the unique patient IDs and a second column matching the IDs to other patient identifying information and/or instructions for notifying other users such as recipients.

The notification module 1022 may be configured to manage one or more sub-modules, components, engines and/or services directed to examples disclosed herein. In some examples, the notification module 1022 may include an initiation engine 1044, an authentication engine 1046, an listening engine 1038, a modification engine 1040, and a routing engine 1042. While these engines are illustrated in FIG. 10 and will be described as performing discrete tasks with reference to the flow charts, it is understood that FIG. 10 illustrates example configurations and other configurations performing other tasks and/or similar tasks as those described herein may be implemented according to the techniques described herein. Other engines, whether embodied in software or hardware, may perform the same tasks as the notification module 1022 or other tasks and may be implemented in a similar fashion or according to other configurations.

The initiation engine 1044 is configured to handle initial communications with a patient who desires to receive notifications or desires to have others receive notifications or her behalf. To this end, the initiation engine 1044 is configured to receive a notification request from a user device of the patient. In the notification request, the patient may identify that she desires that notifications pertaining to her treatment be sent. These notifications may specify one or more decisions made regarding the patient and/or actions performed in relation to responding to the current conditions of the patient. The current conditions may relate to the current conditions of the health of the patient.

The authentication engine 1046 is configured to authorize users which are to receive notifications on behalf of the patient. To this end, the authentication engine 1046 is configured to receive authorization requests from user devices of second users. A particular authorization request may include identifying information of the patient and may be provided by a requesting user. Using this identifying information, the authentication engine 1046 verifies that the requesting user is authorized to receive the notifications. This may include comparing the identifying information in the authorization request with patient record information of the patient. In some examples, the requesting user is only authorized to receive a portion of the notifications. In this manner, the distribution of notifications may be limited to those users (and respective user devices) that are authorized by the patient and the notification service 1002.

The listening engine 1038 is configured to identify a particular patient based at least in part on a message or portion of a message provided by the bus listener 1004 or on information provided directly from one of the user devices 1012. To this end, the listening engine 1038 is configured to initiate the bus listeners 1004. The bus listeners 1004 operate as described herein to identify messages which identify the patient and/or a user device associated with the patient. In one example, the bus listener 1004 receives instructions to monitor de-identified information for a unique patient ID. Once the bus listener 1004 identifies a message corresponding to the unique patient ID, the bus listener 1004 transfers at least a portion of the message to the notification module 1022, where the listening engine 1038 performs one or more operations on the message to identify it (i.e., determine to which patient it belongs). In one example, the listening engine 1038 may make one or more queries to the look-up database 1036 to assist in identifying the message. The queries may request information corresponding to the message received from the bus listener 1004. The listening engine 1038 may receive in return adequate information to match the message to a particular patient. From this information, other components of the notification module 1022 may generate a notification.

The modification engine 1040 may be configured to perform one or more operations on the message received from the bus listener 1004. To this end, the modification engine 1040 may include one or more rule sets to determine how perform its operations to modify the message. For example, rules may be particularized to users, groups of users, and the like. In some examples, a rule may indicate that all identifying information be removed from a message before a notification is generated. Another rule may indicate whether the message should be translated from one language to another language prior to being provided to the device 1012. Thus, the rules may reference user information, including user settings, retained in the user information database 1034. Any of the modification rules may be user-defined, machine-defined, learned, generated, or otherwise created. In some examples, the rules may ensure compliance with regulations which limit the amount of health information that may be exchanged using unsecured communication channels. In some examples, the modification engine 1040, in accordance with the rules or otherwise, performs a language translation (e.g., from Russian to English), performs a format translation (e.g., from a first proprietary format to a vanilla or homogenized format), performs a machine language translation (e.g., from a first machine language to a second machine language), performs a conversion (e.g., from one unit system to a second unit system), performs a mathematic function (e.g., rounds numeric information to a certain number of significant digits), and the like. In some examples, such modification may be helpful to providing accurate notifications to the user devices 1012.

The routing engine 1042 may be configured to generate notifications in accordance with the techniques described herein. In some examples, the routing engine 1042 generates notifications in accordance with one or more notification rules. The notification rules may indicate characteristics of the notifications that will be sent to the user devices 1012. For example, the notification rules may indicate the number of characters supported by a particular user device 1012. In some examples, the notification rules include generic rules and specific rules. Any of the notification rules may be user-defined, machine-defined, learned, generated, or otherwise created. Once a notification is generated, the routing engine 1042 transmits the notification to the authorized user device (e.g., the user device 1012). In some examples, the routing engine 1042 transmits the notification to the message vendor 1016 and the message vendor provides the notification to the user device 1012.

Figure 11:
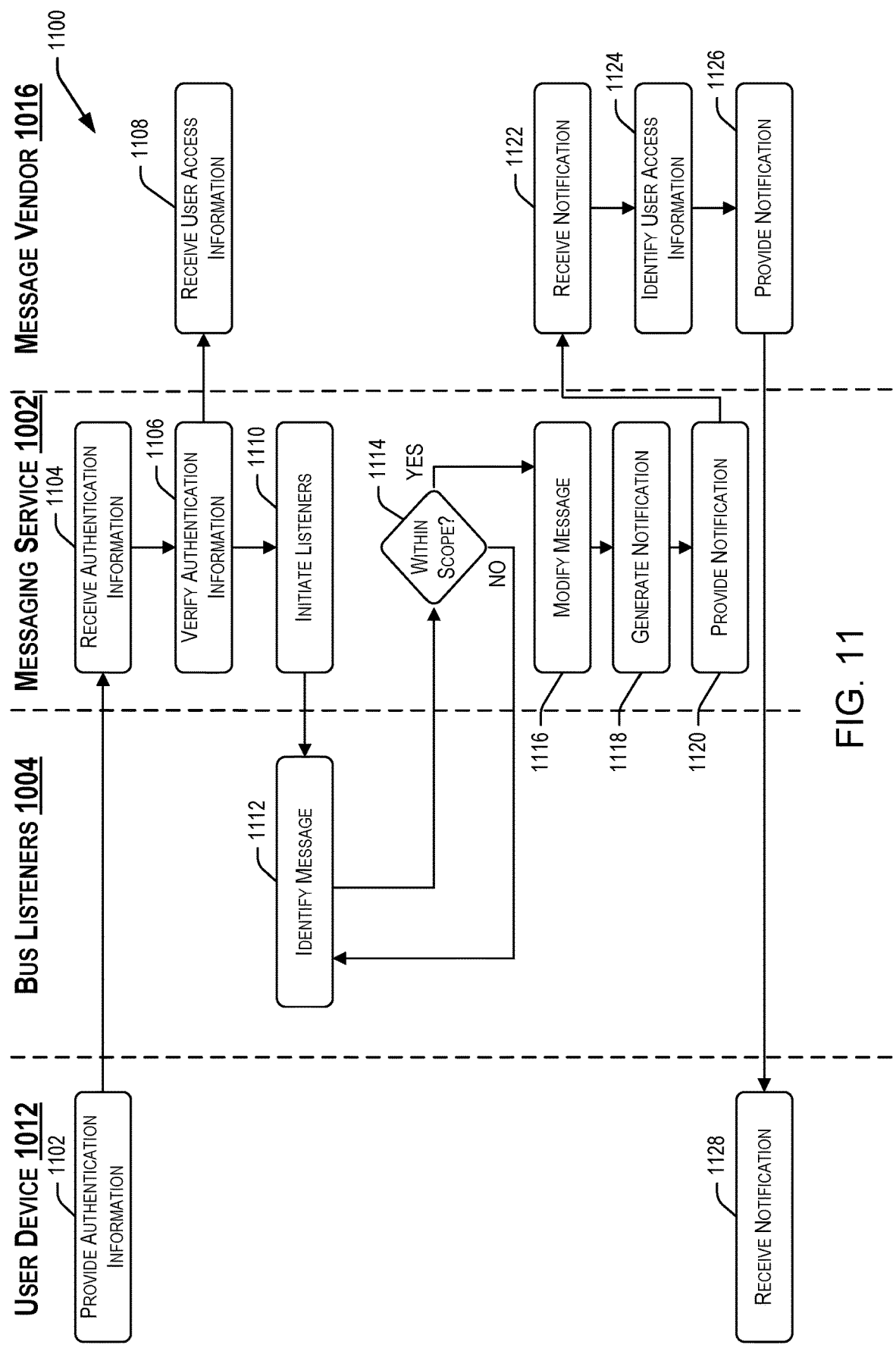
FIG. 11 is a flow diagram depicting example acts for implementing techniques relating to initiating message listening and routing message content to authorized user devices as described herein may be implemented, according to at least one example.

Turning now to FIG. 11, in which is illustrated process 1100 illustrating an example flow diagram depicting techniques relating to providing notifications to user devices in accordance with at least one example. The illustrated flow diagram includes areas identified by the user device 1012, one or more bus listeners 1004, the notification service 1002, and the message vendor 1016. While certain acts will be discussed within each of the respective areas, it is understood that the same acts may take place in different areas or by different entities.

The process 1100 begins at 1102 where the user device 1012 provides authentication information to the notification service 1002. When the user of the user device 1012 is a patient, the authentication information may capable of identifying the user. When the user of the user device 1012 is a person other than the patient (e.g., a family member, friend, medical professional, or other person desiring to receive notifications regarding the patient), the authorization information may be capable of identifying the user. For example, the authentication information may include identifying information of the patient. Such information may have been previously provided to the user of the user device 1012 prior to the user providing the authentication information at 1102. For example, the patient may sign up with the notification service 1002 by sending a notification request to the notification service 1002 (not shown). The notification service 1002 may indicate in one of the data stores (e.g., the data store 1032) that the patient desires to receive notifications and/or desires that others receive notifications.

At 1104, the authentication information 1104 is received by the notification service 1002. At 1106, the notification service 1002 verifies the authentication information. In some examples, verifying the authentication information may include comparing the authentication information (e.g., a unique patient ID, a portion of a unique patient ID, a date of birth of the patient 118, and/or any other types of information described herein) with similar types of information in the data store 1032 to verify that the information provided by the patient or non-patient user matches the information on record for the patient. This may include the notification service 1002 comparing the authentication information (e.g., a date of birth of the patient and unique patient ID of the patient) received with lists of dates of birth and lists of unique patient IDs stored in the data store 1032. Upon verification of the authentication information at 1106, a portion of the verified information is provided to the message vendor 1016 in the form of user access information at 1108. The user access information indicates suitable information such that the message vendor 1016 can contact the user on the user device 1012. Thus, in some examples, the user access information may include a phone number, email address, or other form of contact information of the user such that the message vendor 1016 can later send notifications to the user.

In some examples, at 1108, process 1100 receives user access information. In some examples, the user access information is received by the message vendor 1016 independent of the verification at 1106. For example, the notification service 1002 may compile a list of phone numbers for user who have requested notifications. The notification service 1002 may provide this list of phone numbers to the message vendor 1016 at any time prior to when the message vendor 1016 sends out a notification to one of the users. In some examples, the user access information is provided to the message vendor 1016 in connection with a notification that is to be sent to the user device 1012 (e.g., at 1120).

At 1110, the process 1100 initiates listeners. In some examples, the notification service 1002 initiates the listeners at 1110. As described herein, the listeners may be embodied hardware, software, or any combination of hardware and software. The listeners may be configured to monitor messages that flow over a messaging bus and retrieve certain messages that they are listening for. In some examples, the listeners may be configured to provide messages or a portion of messages from the messaging bus. The messages may be generated for any number of reasons. For example, the messages may be generated in response to one more events including, for example, an adjustment to a medical record of the patient, an adjustment to a location of the patient in a medical care facility, an order of a medical test for the patient, an order of a prescription for the patient, a commencement of a medical procedure on the patient, a conclusion of a medical procedure on the patient, a change in a condition of the patient, or any other event. In some examples, the one or more events include an update to a medical record of the patient. In some examples, a medical care professional may have entered a note into the medical record of the patient pertaining to the treatment of the patient. The entry of this note (e.g., a change in the medical record) may prompt a message to flow over the messaging hub. At 1112, one of the bus listeners 1004 may identify the message. Identifying the message may include the bus listeners 1004 identifying that a particular message includes information identifying the patient.

At 1114, the process 1100 determines whether the identified message is the type of message that should be reported out to the user. In some examples, the message service 1002 makes this determination. The bus listeners 1004 may identify many messages which identify the patient, only some of which may be relevant to the user or even reportable to the user. For example, a message that indicates lab results for the patient may not be reportable because it is prohibited by law. In some examples, the determination at 1114 is performed in accordance with one or more rules. At least some of the rules may be generic to all patients and at least some rules may be specific to particular users. In some example, the message may be irrelevant to the user and may therefore not be included in a notification.

If the determination at 1114 is NO, the process 1100 returns to 1112 where the bus listeners 1004 identify messages. If the determination at 1114 is YES, the process 1100 continues to 1116 where the message is modified. As described herein, the message may be translated, shortened, altered, or otherwise adjusted at 1116. In some examples, even if a message is within the scope at 1114, the message may still be modified at 1116. In some examples, this may be desirable such that the notifications that are provided are consistent and comply with user preferences. In some examples, the message may include medical-related information such as, for example, personal health information (PHI) (i.e., any information about health status, provision of health care, or payment that can be linked to the patient) and also includes any of the following information capable of identifying the patient: names, geographic identifiers, dates directly relating to the patient 118, phone numbers, fax numbers, email addresses, social security numbers, medical record numbers, health insurance beneficiary numbers, account numbers, certificate/license numbers, vehicle identifiers and serial numbers, device identifiers and serial numbers, web Uniform Resource Locators, Internet Protocol addresses, biometric identifiers (e.g., finger, retinal, and voice prints), full face photographic images and any comparable images, and any other unique identifying number, characteristic, or code.

At 1118, the process generates a notification. In some examples, the notification service 1002 generates the notification. In some examples, the notification is generated in accordance with one or more generation rules. The rules may indicate formats for notifications including, for example, character limits, supported formats and characters, languages, etc. For example, in some cases, translation of the message occurs when the notification is generated at 1118 and not at 1116 when the message is modified. In some examples, personal health information is removed from the message as the notification is generated. In this manner, the notification is devoid of personal health information.

At 1120, the process provides the notification. In some examples, the notification service 1002 provides the notification. Providing the notification may include the notification service transferring the notification to the message vendor 1016. In some examples, the message vendor 1016 and the notification service 1002 are connected via a virtual private network. In any event at 1122, the process 1100 receives the notification. In some examples, the message vendor 1016 receives the notification. The notification may include information about the patient. For example, the notification may indicate a status of the patient's treatment and many other like notifications as described herein.

At 1124, the process 1100 identifies user access information. In some examples, the message vendor 1016 identifies the user access information. In some examples, the user access information has been provided prior to the notification being received at 1122. In some examples, the notification at 1122 includes the user access information. In this example, the message vendor may only be given a minimum amount of information to send the notification (e.g., the notification and a phone number to send the notification to). In this manner, the identity of the patient and the user may be protected from inadvertent disclosure by the message vendor 1016. In some examples, the message vendor 1016 is included as part of the notification service 1002. In this example, the notification service 1002 may generate and send the message to the user device 1012. At 1126, the process 1100 provides the notification. In some examples, the message vendor 1016 provides the notification. In some examples, providing the notification may include adjusting the notification to comply with a messaging standard and sending the notification to the user device 1012. In some examples, the message vendor 1016 performs on or more encryption techniques on the notification prior to sending the notification to the user device at 1128.

At 1128, the process 1100 receives the notification. In some examples, the user device 1012 receives the notification. Receiving the notification may include receiving the notification in the form of an SMS, MMS, email, or other electronic messaging service. In some examples, receiving the notification includes performing one or more decryption techniques on the notification. In some examples, when suitable encryption and decryption techniques are used, personal health information may be shared in notifications.

Figure 12:
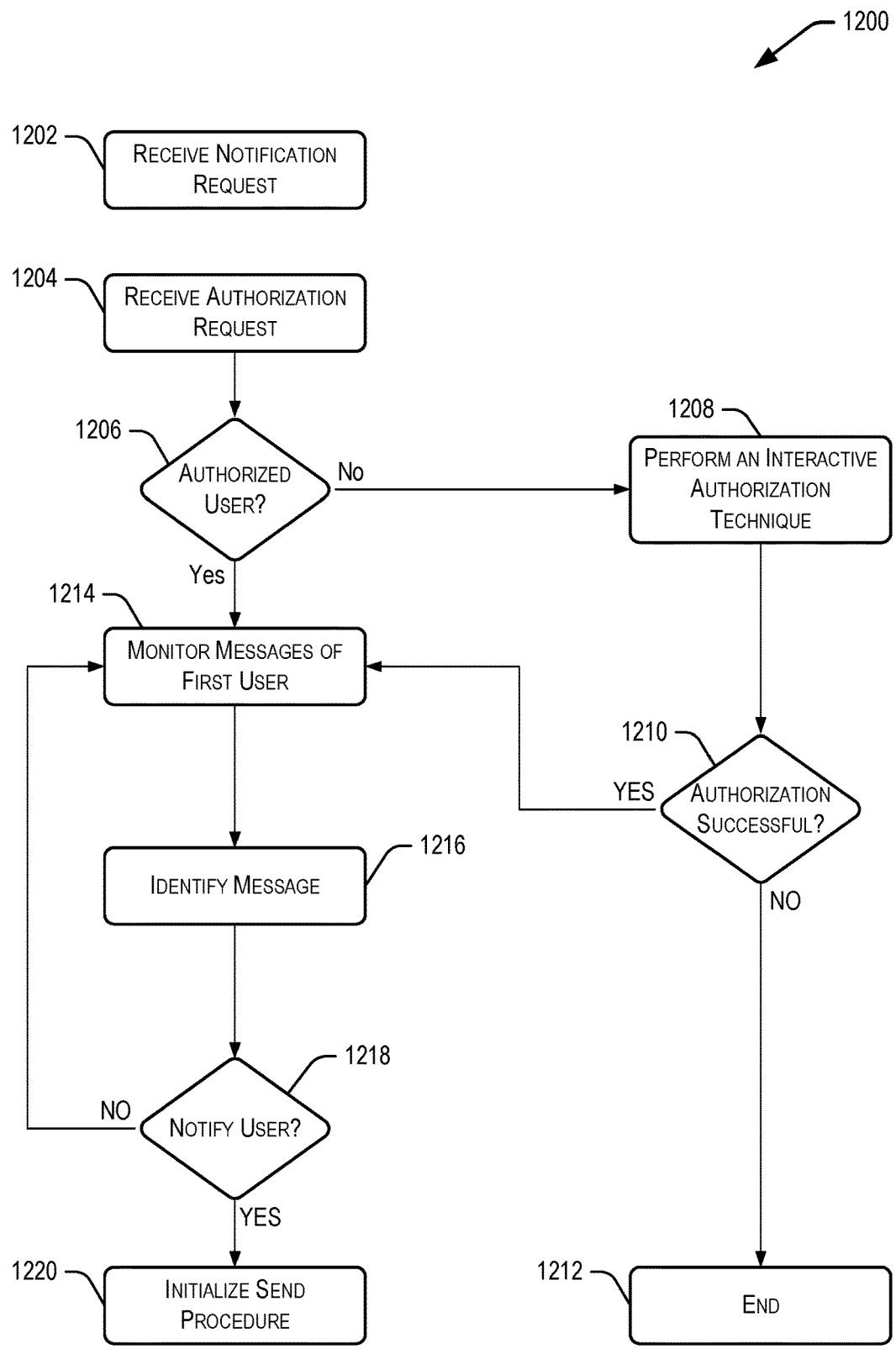
FIG. 12 is a flow diagram depicting example acts for implementing techniques relating to initiating message listening and routing message content to authorized user devices as described herein may be implemented, according to at least one example.

Turning next to example acts and/or procedures that may be performed using techniques described herein, in accordance with at least one example. FIG. 12 depicts process 1200 including example acts for techniques relating to providing notifications to user devices in accordance with at least one example. Some or all of the process 1200 (or any other processes described herein, or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory. The notification module 1022 (FIG. 10) of the notification service 1002 (FIG. 10) may perform the process 1200 of FIG. 12. The process 1200 begins at 1202 by receiving a notification request. In some examples, receiving the notification request is performed by the initiation engine 1044 (FIG. 10). The notification request may be provided by a first user device of a first user. The first user may be a patient of a medical care provider. The notification request may indicate that one or more second user devices be provided with notifications specifying one or more decisions made or actions performed in relation to responding to current conditions pertaining to the first user. In some examples, the notification request does not identify particular user devices, but instead identifies particular users which may receive notifications. In some examples, the notification request simply requests that notifications be provided to all authorized users.

At 1204, the process 1200 receives an authorization request. In some examples, receiving the authorization request is performed by the authentication engine 1046 (FIG. 10). The authorization request may be received from a second user device of the one or more second user devices identified by the notification request. A second user of the second user device may be a relative or friend of the first user (e.g., the patient), or may otherwise be associated with the first user. In some examples, the second user is a medical professional treating the first user.

At 1206, the process 1200 determines whether the second user is authorized. In some examples, determining whether the second user is authorized is performed by the authentication engine 1046. In some examples, the authorization request includes identifying information capable of identifying the first user. In some examples, the first user provides the second user with the identifying information prior to the second user sending the authorization request. At least a portion of the identifying information may be used to determine that the second user device (and second user) is authorized to receive the notifications. For example, when the identifying information provided by the second user matches corresponding information in a record of the user, the second user may be authorized. In some examples, determining whether the second user is authorized may include comparing a unique device identifier with a list of device identifiers of authorized devices. In some examples, the authorization request includes a unique authorization code (e.g., a randomly-generated alphanumeric code). A corresponding code may have been previously generated when the first user provided the notification request. Using the unique code, the authorization code may be compared to the earlier-generated code to determine whether the codes match.

If the answer at 1206 is NO, the process 1200 continues to 1208 where the process 1200 performs an interactive authorization technique. In some examples, performing the interactive authorization technique may be performed by the authentication engine 1046. In some examples, this may include transmitting a communication to the second user device that requests a response. For example, the authentication engine 1046 may interact with the second user device in manner to ensure that the second user device (and second user) are authorized. For example, the authentication engine 1046 may pose one or more questions, which the second user of the second user device must answer correctly prior to being authorized.

Like at 1206, at 1210, the process 1200 determines whether authorization of the second user has been successful. If NO, the process 1200 continues to 1212 where the process ends. If YES, the process 1200 continues to 1214 where records of the first user are monitored. Similarly, if the user is authorized at 1206, the process 1200 continues to 1214 where records of the first user are monitored. In some examples, monitoring records of the first user may be performed by the listening engine 1038 (FIG. 10). This may include, for example, initiating one or more listeners to monitor messages flowing over a messaging bus to identify those messages which identify the first user or the first user device. In some examples, the message may not identify the first user, but may otherwise be relevant to the treatment of the first user. For example, the messages may be generic for all user (e.g., emergency messages, generic advertisements, and the like).

At 1216, the process 1200 identifies a message. In some examples, identifying a message may be performed by the listening engine 1038. In some examples, identifying a message may include identifying a change in a record of the first user. For example, identifying the record change may include recognizing a difference in medical record information. For example, if at T-1 the first user's (e.g., the patient) blood pressure was 120/80, but at a later time, T-2, the same user's blood pressure is 139/89. The record change may be identified by comparing the two entries. In some examples, identifying a message may include identifying any change or entry to the first user's record. In some examples, identifying the message includes determining whether a change in the first user's record is the type of change that should be reported out to the user. For example, in the blood pressure example, the increase from 120/80 to 139/89 is within prehypertension range. However, depending on sets of notification rules (descried herein), the system can be configured to notify users on blood pressure changes when the changed record is above stage 1 hypertension (e.g., >140/90).

In some examples, identifying the message may include comparing an amount of change of a medical record associated with the message compared to a predetermined value. In some examples, the change is an amount of words added or subtracted from the medical record. In other words, in some examples, it is inefficient to determine the substance of the change. Rather, it is more efficient to determine the amount of change based on some objective factor (e.g., increase or decrease in number of words, letters, or numbers, changes to numbers, addition or deletion of records, changes in events representable in binary format (e.g., admitted/ discharged, in surgery/out of surgery), etc.). In this manner, the service efficiently notifies users.

At 1218, the process 1200 determines whether to notify the second user. In some examples, determining whether to notify the second user may be performed by the routing engine 1042. Determining whether to notify the second user may include accessing one or more notification rules to determining if the identified message, which may include a change to the first user's record, should be reported out to the second user. In some examples, the notification rules are specific to the first user. Some rules may be generally applicable to all users. Such rules may indicate, under what circumstances, if any, identifying information may be included in notification. In some examples, higher and lower levels of details may be provided to different users. For example, a family member may want a different level of detail than a medical care professional. In some examples, even minute details may be relevant to the medical professional, while the family member may only want to receive notifications that indicate bigger items.

If the answer at 1218 is NO, the process 1200 returns to 1214 to monitor messages of the first user. If the answer at 1218 is YES, the process 1200 proceeds to 1220 to initialize a send procedure. Initializing the send procedure may be performed by the routing engine 1042. The discussion of possible send procedures continues with reference to FIG. 13.

Figure 13:
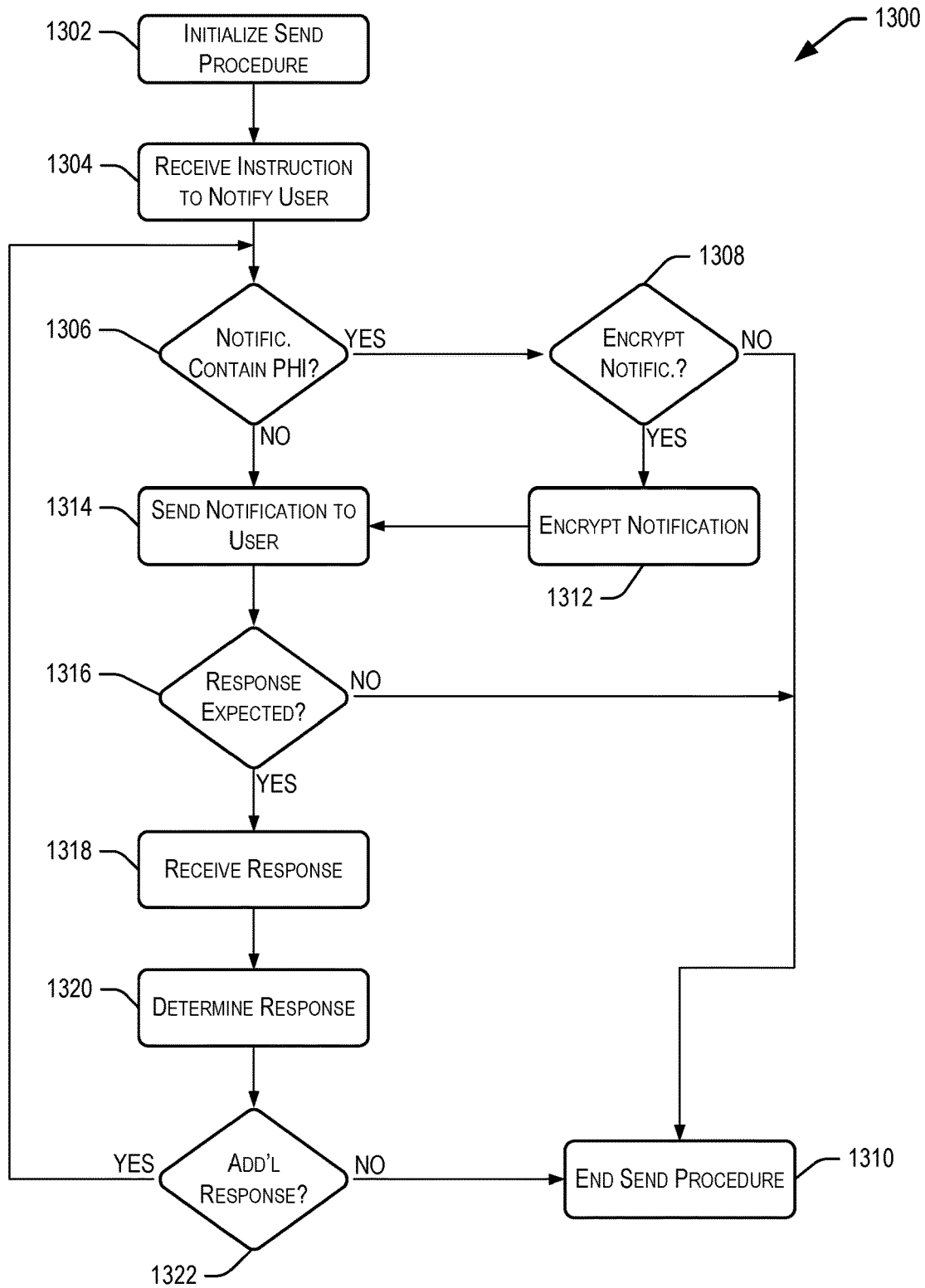
FIG. 13 is a flow diagram depicting example acts for implementing techniques relating to initiating message listening and routing message content to authorized user devices as described herein may be implemented, according to at least one example.

FIG. 13 depicts process 1300 including example acts for techniques relating to providing notifications to user devices in accordance with at least one example. The notification module 1022 (FIG. 10) of the notification service 1002 (FIG. 10) may perform the process 1300 of FIG. 13. The process 1300 begins at 1302 by initializing a send procedure. As described with reference to FIG. 12, at 1302, the second user may already have been authorized. In some examples, initializing the send procedure may be performed by the routing engine 1042 (FIG. 10).

At 1304, the process 1300 receives instructions to notify one or more users of changes to medical record information. In some examples, receiving instructions may be performed by the routing engine 1042. In some examples, the instructions were previously received and stored in association with the first user (e.g., the patient).

At 1306, the process 1300 determines whether a notification (to be sent to users) include some form of personal health information (PHI). If the notification does contain PHI, the process 1300 continues to 1308 where the process determines whether to encrypt the notification. In some examples, determining whether to encrypt the notification may be performed by the modification engine 1040 (FIG. 10). If the answer at 1306 is NO, the process 1300 continues to 1310 where the process ends the send procedure. If the answer at 1308 is YES, the process 1300 continues to 1312, where the notification is encrypted using one or more encryption techniques described herein. In some examples, encrypting may be performed by the modification engine 1040.

The process 1300 then continues to 1314 where the process 1300 sends the notification to the second user. In some examples, send the notification may be performed by the routing engine 1042. In some examples, sending the notification to the second user may include sending the message via one or more vendors (e.g., the message vendor 1016). In other examples, sending the notification to the second user may include sending the notification directly via text message, via email, via an application running on a user device, or the like.

At 1316, the process 1300 determines whether a response to the notification is expected. In some examples, determining whether the response to the notification is expected is performed by the authentication engine 1046 (FIG. 10). A response may be expected if the notification included a question. For example, a notification may indicate that the first user has finished a procedure and is ready to be picked up and may request that the second user indicate whether the second user can pick up the first user within a certain time period. If a response is not expected, the process 1300 continues to 1310 where the procedure ends. If, on the other hand, a response is expected, the process 1300 continues to 1318 where a response is received. In some examples, receiving the response may be performed by the routing engine 1042. Receiving the response may include receiving a response from the second user via SMS, via email, via an application running on the mobile device, or the like.

At 1320, the process 1300 determines the response. In some examples, determining the response may be performed by the authentication engine 1046. Determining the response may include determining whether the response received at 1318 was responsive to the notification sent at 1314. In some examples, the response is determined to be non-responsive when the received response does not answer the questions posed in the notification, is received after a predetermined time, or the like.

At 1322, the process 1300 determines whether additional responses are expected. In some examples, determining whether additional response are expected may be performed by the authentication engine 1046. If NO, the process 1300 ends at 1310. If YES, the process 1300 feeds back into the flow between 1304 and 1306. In this manner, the process 1300 continues to communicate back and forth with the user.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed:

1. A system to route medical message content from a plurality of different sources for access by a plurality of different endpoint devices, the system comprising:
   one or more network interfaces;
   memory configured to store computer-executable instructions; and
   one or more servers comprising one or more processors in communication with the memory and configured to execute the computer-executable instructions to perform actions comprising:
      monitoring for medical messages transmitted from the plurality of different sources corresponding to electronic devices communicably couplable via a network comprising a messaging bus;
      processing a first message from a first electronic device of the electronic devices;
      identifying a first identifier corresponding to a first recipient for the first message, the first recipient corresponding to a first endpoint of a plurality of different endpoints;
      identifying a first notification method selected from a plurality of notification methods provided at least in part by a notification service for transmission of a first notification based at least in part on a first set of rules comprising notification rules that are machine-learned and specific to the first recipient;
      when a communication channel corresponding to the first notification method is unsecured:
         modifying the first message with a first set of modification operations, the modifying comprising processing the first message to comply with regulations limiting health information exchanged using unsecured communication channels;
         generating the first notification in accordance with the first notification method selected from the plurality of notification methods; and
         causing transmission of the first notification comprising a portion of the first message in accordance with the first notification method;
      processing a second message from the first electronic device or a second electronic device of the electronic devices;
      identifying a second identifier corresponding to a second recipient for the second message, the second recipient corresponding to a second endpoint of the plurality of different endpoints;
      authorizing the second recipient by the notification service using authorized identification information associated with the second recipient that was previously received by the notification service from the second recipient;
      identifying a second notification method selected from the plurality of notification methods for transmission of a second notification based at least in part on a second set of rules comprising notification rules that are machine-learned and specific to the second recipient;
      when a communication channel corresponding to the second notification method is secured:
         modifying the second message with a second set of modification operations, the modifying comprising processing the second message to determine at least a portion of the second message to pull for inclusion in the second notification, where the second set of modification operations differs from the first set of modification operations at least in that protected health information is not removed from the portion of the second message;
         generating the second notification in accordance with the second notification method selected from the plurality of notification methods; and
         causing transmission of the second notification comprising the portion of the second message in accordance with the second notification method.

2. The system to route message content from a plurality of different sources for access by a plurality of different endpoint devices as recited in claim 1, where the generating the first notification comprises including the portion of the first message in the first notification but not another portion of the first message.

3. The system to route message content from a plurality of different sources for access by a plurality of different endpoint devices as recited in claim 2, where the generating the first notification comprises performing language translation of at least part of the first message from a first language to a second language, and the generating the second notification comprises performing language translation of at least part of the second message to a third language.

4. The system to route message content from a plurality of different sources for access by a plurality of different endpoint devices as recited in claim 3, where:
   the causing transmission of the first notification comprises providing the first notification and a first destination indicator corresponding to the first recipient to a second system, and instructing the second system to transmit the first notification using the first notification method; and
   the causing transmission of the second notification comprises providing the second notification and a second destination indicator corresponding to the second recipient to the second system or a third system, and instructing the second system or the third system to transmit the second notification using the second notification method.

5. The system to route message content from a plurality of different sources for access by a plurality of different endpoint devices as recited in claim 4, where the second system is a messaging service, and the third system is a different messaging service.

6. A method for routing medical message content from a plurality of different sources for access by a plurality of different endpoint devices, the method comprising:
   monitoring for medical messages transmitted from the plurality of different sources corresponding to electronic devices communicably couplable via a network comprising a messaging bus;
   processing a first message from a first electronic device of the electronic devices;
   identifying a first identifier corresponding to a first recipient for the first message, the first recipient corresponding to a first endpoint of a plurality of different endpoints;
   identifying a first notification method selected from a plurality of notification methods provided at least in part by a notification service for transmission of a first notification based at least in part on a first set of rules comprising notification rules that are machine-learned and specific to the first recipient;
   when a communication channel corresponding to the first notification method is unsecured:
      modifying the first message with a first set of modification operations, the modifying comprising processing the first message to comply with regulations limiting health information exchanged using unsecured communication channels;
      generating the first notification in accordance with the first notification method selected from the plurality of notification methods; and
      causing transmission of the first notification comprising a portion of the first message in accordance with the first notification method;
   processing a second message from the first electronic device or a second electronic device of the electronic devices;
   identifying a second identifier corresponding to a second recipient for the second message, the second recipient corresponding to a second endpoint of the plurality of different endpoints;
   authorizing the second recipient by the notification service using authorized identification information associated with the second recipient that was previously received by the notification service from the second recipient;
   identifying a second notification method selected from the plurality of notification methods for transmission of a second notification based at least in part on a second set of rules comprising notification rules that are machine-learned and specific to the second recipient;
   when a communication channel corresponding to the second notification method is secured:
      modifying the second message with a second set of modification operations, the modifying comprising processing the second message to determine at least a portion of the second message to pull for inclusion in the second notification, where the second set of modification operations differs from the first set of modification operations at least in that protected health information is not removed from the portion of the second message;
      generating the second notification in accordance with the second notification method selected from the plurality of notification methods; and
      causing transmission of the second notification comprising the portion of the second message in accordance with the second notification method.

7. The method for routing message content from a plurality of different sources for access by a plurality of different endpoint devices as recited in claim 6, where the generating the first notification comprises including the portion of the first message in the first notification but not another portion of the first message.

8. The method for routing message content from a plurality of different sources for access by a plurality of different endpoint devices as recited in claim 7, where the generating the first notification comprises performing language translation of at least part of the first message from a first language to a second language, and the generating the second notification comprises performing language translation of at least part of the second message to a third language.

9. The method for routing message content from a plurality of different sources for access by a plurality of different endpoint devices as recited in claim 8, where:
   the causing transmission of the first notification comprises providing the first notification and a first destination indicator corresponding to the first recipient to a second system, and instructing the second system to transmit the first notification using the first notification method; and
   the causing transmission of the second notification comprises providing the second notification and a second destination indicator corresponding to the second recipient to the second system or a third system, and instructing the second system or the third system to transmit the second notification using the second notification method.

10. The method for routing message content from a plurality of different sources for access by a plurality of different endpoint devices as recited in claim 9, where the second system is a messaging service, and the third system is a different messaging service.

11. One or more computer-readable storage devices for storing computer-executable instructions that, when executed by one or more computer systems, configure the one or more computer systems to perform operations for routing medical message content from a plurality of different sources for access by a plurality of different endpoint devices, the operations comprising:
  monitoring for medical messages transmitted from the plurality of different sources corresponding to electronic devices communicably couplable via a network comprising a messaging bus;
  processing a first message from a first electronic device of the electronic devices;
  identifying a first identifier corresponding to a first recipient for the first message, the first recipient corresponding to a first endpoint of a plurality of different endpoints;
  identifying a first notification method selected from a plurality of notification methods provided at least in part by a notification service for transmission of a first notification based at least in part on a first set of rules comprising notification rules that are machine-learned and specific to the first recipient;
  when a communication channel corresponding to the first notification method is unsecured:
    modifying the first message with a first set of modification operations, the modifying comprising processing the first message to comply with regulations limiting health information exchanged using unsecured communication channels;
    generating the first notification in accordance with the first notification method selected from the plurality of notification methods; and
    causing transmission of the first notification comprising a portion of the first message in accordance with the first notification method;
  processing a second message from the first electronic device or a second electronic device of the electronic devices;
  identifying a second identifier corresponding to a second recipient for the second message, the second recipient corresponding to a second endpoint of the plurality of different endpoints;
  authorizing the second recipient by the notification service using authorized identification information associated with the second recipient that was previously received by the notification service from the second recipient;
  identifying a second notification method selected from the plurality of notification methods for transmission of the second notification based at least in part on a second set of rules comprising notification rules that are machine-learned and specific to the second recipient;
  when a communication channel corresponding to the second notification method is secured:
    modifying the second message with a second set of modification operations, the modifying comprising processing the second message to determine at least a portion of the second message to pull for inclusion in a second notification, where the second set of modification operations differs from the first set of modification operations at least in that protected health information is not removed from the portion of the second message;
    generating the second notification in accordance with the second notification method selected from the plurality of notification methods; and
    causing transmission of the second notification comprising the portion of the second message in accordance with the second notification method.

12. The one or more computer-readable storage devices as recited in claim 11, where the generating the first notification comprises including the portion of the first message in the first notification but not another portion of the first message.

13. The one or more computer-readable storage devices as recited in claim 12, where the generating the first notification comprises performing language translation of at least part of the first message from a first language to a second language, and the generating the second notification comprises performing language translation of at least part of the second message to a third language.

14. The one or more computer-readable storage devices as recited in claim 13, where:
  the causing transmission of the first notification comprises providing the first notification and a first destination indicator corresponding to the first recipient to a second system, and instructing the second system to transmit the first notification using the first notification method; and
  the causing transmission of the second notification comprises providing the second notification and a second destination indicator corresponding to the second recipient to the second system or a third system, and instructing the second system or the third system to transmit the second notification using the second notification method.

* * * * *